US009301885B2

(12) United States Patent
Komatsu et al.

(10) Patent No.: US 9,301,885 B2
(45) Date of Patent: Apr. 5, 2016

(54) ABSORBENT ARTICLE

(75) Inventors: Shimpei Komatsu, Kagawa (JP); Yuki Noda, Kagawa (JP); Mitsuhiro Wada, Kagawa (JP); Akira Hashino, Kagawa (JP); Hideyuki Kinoshita, Kagawa (JP); Masashi Nakashita, Kagawa (JP); Ichiro Wada, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 217 days.

(21) Appl. No.: 14/114,147

(22) PCT Filed: Apr. 23, 2012

(86) PCT No.: PCT/JP2012/061505
§ 371 (c)(1),
(2), (4) Date: Oct. 25, 2013

(87) PCT Pub. No.: WO2012/147981
PCT Pub. Date: Nov. 1, 2012

(65) Prior Publication Data
US 2014/0052086 A1    Feb. 20, 2014

(30) Foreign Application Priority Data

Apr. 28, 2011 (JP) ................................ 2011-102231
Sep. 2, 2011 (JP) ................................ 2011-192148

(51) Int. Cl.
*A61F 13/42* (2006.01)
*A61F 13/511* (2006.01)
(Continued)

(52) U.S. Cl.
CPC ............... *A61F 13/42* (2013.01); *A61F 13/472* (2013.01); *A61F 13/511* (2013.01); *A61F 2013/51377* (2013.01)

(58) Field of Classification Search
CPC .................... A61F 13/511; A61F 2013/51377
See application file for complete search history.

(56) References Cited

U.S. PATENT DOCUMENTS 3,929,135 A    12/1975  Thompson
4,588,630 A     5/1986  Shimalla
(Continued)

FOREIGN PATENT DOCUMENTS

CN    1432352 A    7/2003
EP    1250940 A1   10/2002
(Continued)

OTHER PUBLICATIONS

Corresponding International Application No. PCT/JP20121061505 Search Report dated Jul. 17, 2012.
(Continued)

*Primary Examiner* — Susan Su
(74) *Attorney, Agent, or Firm* — Hauptman Ham, LLP

(57) ABSTRACT

An absorbent article includes a liquid-permeable top sheet, a liquid-impermeable back sheet, and an absorbent body between the liquid-permeable top sheet and liquid-impermeable back sheet. The top sheet exhibits a color difference in a range of 37-80, based on the L*a*b* color system and measured from a skin contact surface of the top sheet in a liquid dropping test. Further, the top sheet has a color-reducing agent having an IOB of 0.00-0.35, a melting point of no higher than 45° C. and a water solubility of 0.00-0.05 g in 100 g of water at 25° C. The absorbent article is configured to allow a user to visually confirm reduction in residue of highly viscous menstrual blood on the top sheet after its absorption, thereby providing reassurance to the user.

10 Claims, 5 Drawing Sheets

(51) Int. Cl.
*A61F 13/472* (2006.01)
*A61F 13/513* (2006.01)

(56) References Cited

U.S. PATENT DOCUMENTS

| | | | |
|---|---|---|---|
| 4,759,754 A | 7/1988 | Korpman | |
| 4,908,026 A * | 3/1990 | Sukiennik et al. | 604/378 |
| 5,078,710 A | 1/1992 | Suda et al. | |
| 5,334,176 A | 8/1994 | Buenger et al. | |
| 5,344,416 A | 9/1994 | Niihara | |
| 5,614,283 A | 3/1997 | Potnis et al. | |
| 5,650,214 A | 7/1997 | Anderson et al. | |
| 6,153,209 A | 11/2000 | Vega et al. | |
| 6,730,819 B1 | 5/2004 | Pesce | |
| 2001/0029141 A1 | 10/2001 | Mizutani et al. | |
| 2003/0088222 A1 | 5/2003 | Yoshimasa et al. | |
| 2003/0149410 A1* | 8/2003 | Kudo et al. | 604/367 |
| 2003/0198784 A1 | 10/2003 | Mizutani et al. | |
| 2006/0184150 A1 | 8/2006 | Noel | |
| 2006/0276767 A1 | 12/2006 | Ueminami et al. | |
| 2007/0219515 A1 | 9/2007 | Marsh et al. | |
| 2007/0298213 A1 | 12/2007 | Noda et al. | |
| 2007/0298214 A1 | 12/2007 | Noda et al. | |
| 2007/0298220 A1 | 12/2007 | Noda et al. | |
| 2007/0298667 A1 | 12/2007 | Noda et al. | |
| 2007/0298671 A1 | 12/2007 | Noda et al. | |
| 2007/0299416 A1 | 12/2007 | Noda et al. | |
| 2008/0010795 A1 | 1/2008 | Mizutani et al. | |
| 2008/0044622 A1 | 2/2008 | Noda et al. | |
| 2008/0044628 A1 | 2/2008 | Noda et al. | |
| 2008/0045915 A1 | 2/2008 | Noda et al. | |
| 2008/0085399 A1 | 4/2008 | Noda et al. | |
| 2008/0132136 A1 | 6/2008 | Uematsu et al. | |
| 2008/0200894 A1 | 8/2008 | Gatto et al. | |
| 2009/0062761 A1* | 3/2009 | Goerg-Wood et al. | 604/385.01 |
| 2009/0221978 A1 | 9/2009 | Gatto et al. | |
| 2009/0282660 A1 | 11/2009 | Noda et al. | |
| 2010/0069874 A1 | 3/2010 | Noda et al. | |
| 2010/0137824 A1 | 6/2010 | Uematsu et al. | |
| 2010/0191207 A1 | 7/2010 | Oba et al. | |
| 2011/0319851 A1 | 12/2011 | Kudo et al. | |
| 2012/0045620 A1 | 2/2012 | Oba et al. | |
| 2012/0136327 A1* | 5/2012 | Jones | 604/359 |
| 2012/0141742 A1 | 6/2012 | Yamaguchi et al. | |
| 2012/0177889 A1 | 7/2012 | Uematsu et al. | |
| 2012/0196091 A1 | 8/2012 | Mizutani et al. | |
| 2013/0034686 A1 | 2/2013 | Mitsuno | |
| 2013/0137328 A1 | 5/2013 | Mitsuno | |
| 2013/0226123 A1 | 8/2013 | Kudo et al. | |

FOREIGN PATENT DOCUMENTS

| | | |
|---|---|---|
| EP | 1362568 | 11/2003 |
| EP | 1371379 A1 | 12/2003 |
| EP | 2036521 A1 | 3/2009 |
| EP | 2433602 A1 | 3/2012 |
| GB | 2262235 | 6/1993 |
| JP | S57-17081 | 4/1982 |
| JP | S64-34365 | 2/1989 |
| JP | S64-56051 | 3/1989 |
| JP | H01-158954 | 6/1989 |
| JP | 2152920 A | 6/1990 |
| JP | H02-229255 | 9/1990 |
| JP | H05-154176 | 6/1993 |
| JP | H06-5614 | 1/1994 |
| JP | 6502104 A | 3/1994 |
| JP | H07-84697 | 9/1995 |
| JP | H08-510665 | 11/1996 |
| JP | H08-322879 | 12/1996 |
| JP | H10-95810 | 4/1998 |
| JP | H10-510743 | 10/1998 |
| JP | H11-512643 | 11/1999 |
| JP | 2000-510376 | 8/2000 |
| JP | 3091283 | 9/2000 |
| JP | 2000-512886 | 10/2000 |
| JP | 2001-095845 | 4/2001 |
| JP | 2001-129019 | 5/2001 |
| JP | 2001-328191 | 11/2001 |
| JP | 2002-508693 | 3/2002 |
| JP | 3262172 | 3/2002 |
| JP | 2002528174 A | 9/2002 |
| JP | 2002-537904 A | 11/2002 |
| JP | 2003-024372 | 1/2003 |
| JP | 2003-052750 | 2/2003 |
| JP | 2004-500908 | 1/2004 |
| JP | 2004-049529 | 2/2004 |
| JP | 2005-504591 | 2/2005 |
| JP | 2005-095759 | 4/2005 |
| JP | 2005193001 A | 7/2005 |
| JP | 2005-525134 | 8/2005 |
| JP | 2006-501022 1 | 1/2006 |
| JP | 2006-510456 | 3/2006 |
| JP | 2006-115996 | 5/2006 |
| JP | 2006-255051 | 9/2006 |
| JP | 2006-280526 A | 10/2006 |
| JP | 2007-014705 A | 1/2007 |
| JP | 2007-509695 | 4/2007 |
| JP | 2008-002034 | 1/2008 |
| JP | 2008-023311 | 2/2008 |
| JP | 2008-023365 | 2/2008 |
| JP | 2008-025080 | 2/2008 |
| JP | 2008-025081 | 2/2008 |
| JP | 2008-025082 | 2/2008 |
| JP | 2008-025083 | 2/2008 |
| JP | 2008-025084 | 2/2008 |
| JP | 2008-025085 | 2/2008 |
| JP | 2008-029830 A | 2/2008 |
| JP | 2008-503323 | 2/2008 |
| JP | 200825078 A | 2/2008 |
| JP | 200825079 A | 2/2008 |
| JP | 2008-138340 | 6/2008 |
| JP | 2008-144322 | 6/2008 |
| JP | 2008529721 A | 8/2008 |
| JP | 2008-237569 A | 10/2008 |
| JP | 2008229032 A | 10/2008 |
| JP | 2008229033 A | 10/2008 |
| JP | 2008-264084 | 11/2008 |
| JP | 2008-266813 | 11/2008 |
| JP | 2008-541943 | 11/2008 |
| JP | 2008-307179 | 12/2008 |
| JP | 2009-005767 A | 1/2009 |
| JP | 2009-030218 | 2/2009 |
| JP | 2009-201878 | 9/2009 |
| JP | 2009-297048 | 12/2009 |
| JP | 201088822 A | 4/2010 |
| JP | 2010518918 A | 6/2010 |
| JP | 2010-148708 | 7/2010 |
| JP | 2010-526629 A | 8/2010 |
| JP | 2010-285735 | 12/2010 |
| JP | 2010279568 A | 12/2010 |
| JP | 2011-038211 | 2/2011 |
| JP | 2011-074515 | 4/2011 |
| JP | 2011-080178 | 4/2011 |
| JP | 201167484 A | 4/2011 |
| JP | 201172650 A | 4/2011 |
| JP | 2011510801 A | 4/2011 |
| JP | 2011-104059 | 6/2011 |
| JP | 2011-120696 | 6/2011 |
| JP | 4693847 | 6/2011 |
| JP | 2011104001 A | 6/2011 |
| JP | 2011226010 A | 11/2011 |
| JP | 2011226011 A | 11/2011 |
| JP | 2012-050626 | 3/2012 |
| JP | 5122007 | 1/2013 |
| WO | 9301781 A1 | 2/1993 |
| WO | 94/27539 | 12/1994 |
| WO | 96/19173 | 6/1996 |
| WO | 98/55158 | 12/1998 |
| WO | 99/00093 | 1/1999 |
| WO | 99/29274 | 6/1999 |
| WO | 0024351 A1 | 5/2000 |
| WO | 01/045757 | 6/2001 |
| WO | 03/017900 | 3/2003 |
| WO | 03/028776 | 4/2003 |

(56) References Cited

FOREIGN PATENT DOCUMENTS

| WO | 2004/030713 | A1 | 4/2004 |
|---|---|---|---|
| WO | 2004/058119 | | 7/2004 |
| WO | 2005/044164 | | 5/2005 |
| WO | 2006/009996 | | 1/2006 |
| WO | 2006-130646 | | 12/2006 |
| WO | 2008/072675 | | 6/2008 |
| WO | 2008101163 | A2 | 8/2008 |
| WO | 2008/139425 | A1 | 11/2008 |
| WO | 2008-149771 | | 12/2008 |
| WO | 2009/102837 | A2 | 8/2009 |
| WO | 2012/133724 | | 10/2012 |

OTHER PUBLICATIONS

International Search Report mailed Jul. 3, 2012 in corresponding International Application No. PCT/JP2012/058499.
International Search Report mailed Mar. 19, 2013 in corresponding International Application No. PCT/JP2012/082087.
International Search Report mailed Mar. 12, 2013 in corresponding International Application No. PCT/JP2012/082104.
International Search Report mailed Mar. 19, 2013 in corresponding International Application No. PCT/JP2013/054382.
International Search Report mailed May 21, 2014 in corresponding International Application No. PCT/JP2013/054796.
International Search Report mailed Jul. 2, 2013 in corresponding International Application No. PCT/JP2013/058860.
International Search Report mailed Jul. 2, 2013 in corresponding International Application No. PCT/JP2013/058861.
International Search Report mailed Jul. 2, 2013 in corresponding International Application No. PCT/JP2013/058862.
International Search Report mailed Jun. 18, 2013 in corresponding International Application No. PCT/JP2013/058855.
International Search Report mailed May 14, 2013 in corresponding International Application No. PCT/JP2013/058836.
International Search Report mailed May 21, 2013 in corresponding International Application No. PCT/JP2013/058859.
International Search Report mailed Mar. 19, 2013 in corresponding International Application No. PCT/JP2012/082078.
International Search Report mailed Mar. 26, 2013, corresponds to International Application No. PCT/JP2012/082977.
International Search Report mailed Jan. 8, 2013, corresponds to International Application No. PCT/JP2012/075583.
Written Opinion dated Jul. 3, 2012, corresponds to International Application No. PCT/JP2012/058499.
Reply to Written Opinion dated Jan. 30, 2013, corresponds to International Application No. PCT/JP2012/058499.
Atsushi Fujita, "Prediction of Organic Compounds and Organic Conceptual Diagram", Kagaku no Ryoiki (Region of Chemistry), Oct. 1957, p. 719-725, vol. 11, No. 10.

* cited by examiner

ABSORBENT ARTICLE

RELATED APPLICATIONS

The present application is a National Phase of International Application Number PCT/JP2012/061505, filed Apr. 23, 2012, and claims priority to Japanese Application Number 2011-102231, filed Apr. 28, 2011 and Japanese Application Number 2011-192148, filed Sep. 2, 2011.

TECHNICAL FIELD

The present disclosure relates to an absorbent article.

BACKGROUND ART

As the basic performance of absorbent articles, such as sanitary napkins and panty liners has continued to improve with technological development over many years, leakage after absorption of excreta, such as menstrual blood has become a less frequent occurrence than in the past. Recent developments are now directed towards absorbent articles with even higher performance, including a feel similar to underwear, and smoothness of the top sheet even after absorption of excreta, such as menstrual blood. Menstrual blood during menstruation may include highly viscous components of the endometrium, and the top sheet should remain smooth and stick-free (non-sticky) even after absorption of such highly viscous menstrual blood. Highly viscous menstrual blood usually remains on the top sheet in the form of masses, generally leaving the user with a visually unpleasant image.

PTL 1, for example, discloses an absorbent article wherein the top sheet has a lotion coating comprising an emollient and an immobilizing agent. According to PTL 1, the lotion coating is used to prevent residue of menstrual blood on the skin or hair of the user.

PTL 2 teaches the use of a lotion composition comprising at least one compound that is liquid at 25° C. and at least one compound that is solid at 25° C., to reduce the adhesion of excreta and menstrual blood onto human skin. Similar to PTL 1, the purpose of PTL 2 is to prevent residue of menstrual blood on the skin or hair of users.

PTL 3 describes an absorbent article that includes cellulose-based hydrophilic fiber comprising one or more surfactants selected from the group consisting of sugar alkyl ethers and sugar fatty acid esters, at locations other than the skin contact surface. According to PTL 3, the effect of the surfactant is to cause blood entering through the top sheet to contact with the surfactant in a second sheet and/or absorber, thereby altering the viscosity and surface tension of the blood so that it is more easily taken up into the absorber, and so that it is more easily absorbed by a super-absorbent polymer. PTL 4 and PTL 5 also describe absorbent articles comprising such surfactants.

Finally, PTL 6 discloses an absorbent article wherein a polypropyleneglycol material-containing lotion composition is applied onto at least part of the outer surface of a top sheet.

CITATION LIST

Patent Literature

PTL 1 Japanese Unexamined Patent Publication No. 2006-501022
PTL 2 Japanese Unexamined Patent Publication No. 2010-526629
PTL 3 Japanese Unexamined Patent Publication No. 2008-29830
PTL 4 Japanese Unexamined Patent Publication No. 2008-237569
PTL 5 Japanese Unexamined Patent Publication No. 2009-5767
PTL 6 WO2009/102837

SUMMARY OF INVENTION

Technical Problem

The inventors have noted that the technical solutions disclosed in PTL 1 and PTL 2 merely prescribe the use of a lotion coating to prevent residue of menstrual blood and the like on the skin or hair of the user, and do not appear to allow the user to visually detect the menstrual blood migrating into the absorber.

Also, the technical solutions described in PTL 3 to PTL 5 use surfactants in an attempt to alter the viscosity and surface tension of highly viscous menstrual blood and increase the absorption rate of liquids, but do not appear to allow the user to visually confirm the migration of menstrual blood into the absorber and the reduction in the residue of the menstrual blood on the top sheet surface.

PTL 6, likewise, does not appear to allow the user to visually confirm the reduction in menstrual blood on the top sheet surface.

It is therefore an object of this disclosure to provide an absorbent article that allows the user to visually confirm reduction in residue of highly viscous menstrual blood on the top sheet after its absorption, thereby providing reassurance to the user.

Solution to Problem

As a result of diligent research directed toward solving the problems described above, the present inventors have produced an absorbent article comprising a liquid-permeable top sheet, a liquid-impermeable back sheet, and an absorbent body between the liquid-permeable top sheet and liquid-impermeable back sheet, wherein the top sheet exhibits a color difference in the range of 37-80, based on the L*a*b* color system and measured from a skin contact surface of the top sheet in a liquid dropping test.

Advantageous Effects of Invention

The absorbent article of the disclosure allows the user to visually confirm reduction in residue of highly viscous menstrual blood on the top sheet after its absorption, thereby providing reassurance to the user.

DESCRIPTION OF EMBODIMENTS

Figure 1:
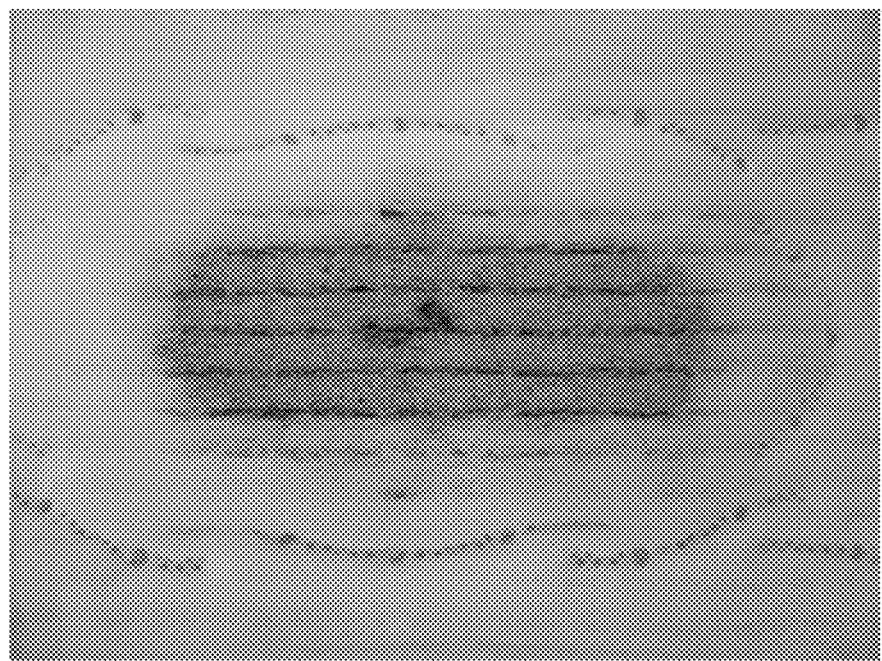
FIG. 1 is an image of sanitary napkin No. 1-1, 40 seconds after completing a second dropping of horse EDTA blood.

The absorbent article of the disclosure will now be explained in detail.

The top sheet of the absorbent article of the disclosure exhibits a color difference in the range of about 37-80, based on the CIE L*a*b* color system and measured from a skin contact surface of the top sheet, in a prescribed liquid dropping test.

As described herein, CIE stands for the International Commission on Illumination, and L*a*b* represents the three coordinates of the color scale. The total color difference $\Delta E$ is a single numerical value which takes into account the differences between the L*, a* and b* values of a sample and a standard.

As used herein, "liquid dropping test" refers to a test conducted in the following manner.

[Procedure for Liquid Dropping Test]

(1) Horse EDTA blood used for the test is dropped on to a white reference board in an amount of 3 mL and allowed to evenly spread, and then the initial coordinates in the CIE L*a*b* color system ($L^*_0$, $a^*_0$, $b^*_0$) are measured. Each of $L^*_0$, $a^*_0$ and $b^*_0$ has a numerical value.

The horse EDTA blood used is 65 mL of horse venous blood, with addition of 0.5 mL of 12% EDTA·2K physiological saline.

(2) A perforated acrylic board (200 mm×100 mm, 125 g, 40 mm×10 mm perforation at the center) is placed at the center section of the top sheet of the absorbent article, and 3 mL of horse EDTA blood at 37±1° C. is dropped with a pipette through the perforation (first dropping).

(3) At 1 minute after the first dropping of horse EDTA blood has been completed, a further 3 mL of horse EDTA blood at 37±1° C. is dropped with a pipette through the acrylic board perforation (second dropping).

(4) 40 seconds after the second dropping of horse EDTA blood has been completed, the post-test coordinates in the CIE L*a*b* color system ($L^*_1$, $a^*_1$, $b^*_1$) are measured at the center section of the top sheet of the absorbent article.

(5) The color difference ($\Delta E$) is calculated by the following formula:

$$\Delta E = \{(L^*_1 - L^*_0)_2 + (a^*_1 - a^*_0)^2 + (b^*_1 - b^*_0)^2\}^{0.5}$$

(6) The measurement is conducted 5 times, and the average value is recorded.

Since horse EDTA blood is used as the reference in this test, a larger color difference ($\Delta E$) corresponds to greater whiteness, and a smaller color difference corresponds to a more red color.

The test is conducted in a thermostatic chamber at 20° C.

The CIE L*a*b* color system coordinates can be measured using any device, such as a CR-300 Chroma Meter by Konica Minolta Holdings, Inc.

The center section of the top sheet is the section of the top sheet which is at the center of the absorbent article in the lengthwise direction and the center of the absorbent article in the widthwise direction.

In the liquid dropping test described above, the top sheet of the absorbent article has a color difference in the range of about 37-80, preferably in the range of about 39-77, and more preferably in the range of about 42-74, based on the CIE L*a*b* color system and measured from a skin contact surface of the top sheet.

If the value for the color difference is less than about 37, which is near the red color of horse EDTA blood, absorbed menstrual blood will be clearly visible from the front side of the top sheet (i.e., the skin contact surface that is adapted to receive bodily discharge thereon), such that it will appear that the absorbent body has not absorbed the menstrual blood, or that the menstrual blood may appear to remain on the surface of the top sheet, creating an undesirable visual image. On the other hand, if the color difference is greater than about 80, which is near the original color of the top sheet (usually white), it will be difficult to discern whether any menstrual blood has been absorbed, thus failing to leave a visual indication that menstrual blood has been absorbed by the absorbent article.

In one embodiment, in a prescribed liquid residue test the top sheet of the absorbent article preferably has a hemoglobin content that is represented by an absorbance of about 0.00-0.10 in a prescribed liquid residue test.

If the top sheet has the hemoglobin content of about 0.00-0.10 as represented by absorbance in the liquid residue test, the top sheet will have a minimal residue of liquid, especially on its surface, after highly viscous menstrual blood has been absorbed and the user will feel more comfortable during its use. Likewise, if the top sheet has the hemoglobin content of about 0.00-0.10 as represented by absorbance in the liquid residue test, the top sheet will have minimal redness, especially on its surface, after highly viscous menstrual blood has been absorbed, so that the user will be able to visually confirm that no liquid is remaining on the top sheet (especially its surface), and the user will also feel more comfortable during its use.

As used herein, "liquid residue test" refers to a test conducted in the following manner.

[Procedure for Liquid Residue Test]

(1) The top sheet is cut into a sample size of 4 cm×4 cm.

(2) The sample is placed on the lower part of a glass-pair filter (filtration area: 9.6 cm$^2$), and then the upper part is placed thereover and the glass-pair filter is anchored with a clamp.

(3) A 3 mL portion of horse EDTA blood at 37±1° C. is dropped over the entire skin contact surface of the top sheet inside the filter and allowed to stand for 1 minute.

(4) The sample is removed from the glass filter and dipped in 5 mL of physiological saline to allow migration of the blood components into the physiological saline.

(5) A portion of the physiological saline into which the blood components have migrated is subjected to centrifugal separation at room temperature for 10 minutes at about 1900 G.

(6) A 200 μL portion of the supernatant of the centrifuged physiological saline is taken on a microtiter plate and used for measurement of absorbance with an optical path length of 1.26 cm and a wavelength of 570 nm, and the amount of eluted hemoglobin due to disruption of erythrocytes is estimated based on this value.

(7) The measurement is conducted 5 times, and the average value is recorded.

The test is conducted in a thermostatic chamber at 20° C.

An example of the commercial products of the glass-pair filter is Glass Filter Folder, with Stainless steel Screen, 47 mm (Catalog No. XX10 047 30) sold by Merck Millipore.

The absorbance can be measured with any desired instrument, such as a Model EL808IU microplate reader by Bio-Tek Instruments, Inc, for example.

As used herein, "horse EDTA blood" is horse blood to which ethylenediaminetetraacetic acid has been added in order to prevent coagulation.

The absorbance at a wavelength of 570 nm is measured because one of the absorption peaks for hemoglobin in erythrocytes is at about 570 nm, and high absorbance at that wavelength indicates a large amount of eluted hemoglobin remaining on the top sheet; in other words, it means that significant liquid remains on the top sheet, thereby giving it a red tint.

The top sheet of the absorbent article preferably has an amount of hemoglobin represented by absorbance of about 0.00-0.10, preferably about 0.00-0.09 and even more preferably about 0.00-0.08, in the liquid residue test described above. If the absorbance is greater than about 0.10, liquid will tend to remain on the top sheet surface during use, creating an unpleasant experience for the user when the article is worn, and the surface of the top sheet will be reddened by menstrual blood, creating a visual image that may result in uneasiness for the user.

In the liquid residue test described above, steps (1) to (4) may be followed by the following steps (5') to (7') to evaluate the blood cell count per 1 g of top sheet.

(5') The physiological saline into which the blood components have migrated is observed under a microscope, and the blood cells are counted with a hemocytometer.

(6') The blood cell count is divided by the initial mass of the sample to calculate the blood cell count per 1 g of top sheet.

(7') The measurement is conducted 5 times, and the average value is recorded.

The test is conducted in a thermostatic chamber at 20° C.

The blood cell count per 1 g of top sheet in the liquid residue test is preferably about from 0 to $30 \times 10^7$/g, more preferably about from 0 to $20 \times 10^7$/g and even more preferably about from 0 to $10 \times 10^7$/g. If the blood cell count per 1 g of top sheet is greater than about $30 \times 10^7$/g, liquid will tend to remain on the top sheet surface during use, creating an unpleasant experience for the user when the article is worn, and the surface of the top sheet will be reddened by menstrual blood, creating a visual image that may result in uneasiness for the user.

If a liquid dropping test for the absorbent article described above results in a color difference in the range of about 37 to 80, based on the L*a*b* color system and measured from a skin contact surface of the top sheet, and if a liquid residue test gives results in which the top sheet has a hemoglobin content represented by absorbance of about 0.00-0.10 and a blood cell count of about $0-30 \times 10^7$/g, then the user will be able to visually confirm that no highly viscous menstrual blood remains on the top sheet after its absorption, thereby reassuring the user. One method of achieving the color difference, hemoglobin content and blood cell count specified above is for the top sheet to include a color-reducing agent with an IOB (Inorganic-Organic Balance) of about 0.00 to 0.35 and a melting point of no higher than about 45° C.

The color-reducing agent may also have a water solubility of about 0.00-0.05 g at 25° C.

The IOB (Inorganic-Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725 which is incorporated by reference herein in its entirety.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso branching | 0 | −10 |
| tert branching | 0 | −20 |
| Light metal (salt) | ≥500 | 0 |
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

The IOB of the color-reducing agent is preferably between about 0.00 and 0.35, more preferably between about 0.00 and 0.30, even more preferably between about 0.00 and 0.25 and yet more preferably between about 0 and 0.20. This is because a lower IOB is associated with higher organicity and higher affinity with blood cells.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example, at a temperature-elevating rate of 10° C./min.

The color-reducing agent preferably has a melting point of no higher than about 45° C., and it may be either liquid or solid at room temperature, or in other words, the melting point may be about 25° C. or higher, or even below about 25° C., and for example, it may have a melting point of about −5° C. or about −20° C.

The color-reducing agent preferably has low vapor pressure. The vapor pressure of the color-reducing agent is preferably about 0.00-0.01 Pa, more preferably about 0.000-0.001 Pa and even more preferably about 0.0000-0.0001 Pa, at 1 atmosphere, 25° C. Considering that the absorbent article is to be used in contact with the human body, the vapor pressure is preferably about 0.00-0.01 Pa, more preferably about 0.000-0.001 Pa and even more preferably about 0.0000-0.0001 Pa, at 1 atmosphere, 40° C. If the vapor pressure is high, gasification may occur during storage and the amount of color-reducing agent may be reduced, and as a consequence problems, such as odor during wear may be created.

The melting point of the color-reducing agent may also differ depending on the weather or on the duration of wear. For example, in regions with a mean atmospheric temperature of up to about 10° C., using a color-reducing agent with a melting point of no higher than about 10° C. may allow the color-reducing agent to rapidly dissolve after excretion of menstrual blood, even if it has been cooled by the ambient temperature.

Also, when the absorbent article is used for a prolonged period of time, the melting point of the color-reducing agent is preferably at the high end of the range of no higher than 45° C. In such a case the color-reducing agent is not easily affected by sweat or friction during wearing, and will not easily migrate even during prolonged wearing.

The water solubility of 0.00-0.05 g may be measured by adding 0.05 g of sample to 100 g of deionized water at 25° C., allowing it to stand for 24 hours, and gently stirring if necessary, and visually evaluating whether or not the sample has dissolved.

As used herein, the term "solubility" used herein in regard to water solubility includes cases where the sample completely dissolves in deionized water to form a homogeneous mixture, and cases where the sample is completely emulsified. As used herein, "completely" means that none of the sample remains in the deionized water.

In the above described art, top sheet surfaces are coated with surfactants in order to alter the surface tension of blood and promote rapid absorption of blood. However, because surfactants generally have high water solubility, the surfactant-coated top sheet is highly miscible with hydrophilic components (such as blood plasma) in the blood and therefore, they tend to cause residue of blood on the top sheet. The color-reducing agent described above has low water solubility and therefore, unlike the surfactants used in the above described art, it does not cause residue of blood on the top sheet and allows rapid migration into the absorbent body.

As used herein, a water solubility in 100 g of water at 25° C. may be simply referred to as "water solubility".

The color-reducing agent may have a water solubility of approximately 0.00 g. Therefore, the lower limit for the water solubility in the color-reducing agent is approximately 0.00 g.

Preferably, the color-reducing agent is selected from the group consisting of following items (i) and (ii), and any combination thereof:

(i) a hydrocarbon; and (ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety.

As used herein, the term "hydrocarbon" refers to a compound composed of carbon and hydrogen, and it may be a chain hydrocarbon, such as a paraffinic hydrocarbon (containing no double bond or triple bond, also referred to as an "alkane"), an olefin-based hydrocarbon (containing one double bond, also referred to as an "alkene"), an acetylene-based hydrocarbon (containing one triple bond, also referred to as an "alkyne"), or a hydrocarbon comprising two or more bonds which may be double bonds or triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear (straight-chain) hydrocarbons and branched hydrocarbons.

When two or more oxy groups (—O—) are inserted between the compounds of (ii) above, the oxy groups (—O—) are not adjacent to each other, or in other words, the compounds according to (ii) do not include compounds with contiguous oxy groups (also known as "peroxides").

When two or more carbonyl groups (—CO—) are inserted between the compounds of (ii) above, the carbonyl groups (—CO—) may not be adjacent to each other.

More preferably, the color-reducing agent is selected from the group consisting of following items (i') and (ii'), and any combination thereof:

(i') a hydrocarbon; and (ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety.

When 2 or more same or different bonds are inserted between a compound of (ii'), that is, when 2 or more bonds, each selected from the group consisting of carbonyl bonds (—CO—), ester bonds (—COO—), carbonate bonds (—OCOO—) and ether bonds (—O—) are inserted between a compound of (ii'), the bonds are not adjacent to each other, and at least one carbon atom lies between each of the bonds.

Also, the color-reducing agent preferably has a polar group with a large inorganic value, such as a carboxyl group (—COOH), hydroxyl group (—OH) or the like. This will result in a larger IOB value and greater hydrophilicity.

Even more preferably, the color-reducing agent is selected from the group consisting of following items (A)-(E), and any combination thereof:

(A) a complete ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;

(B) a complete ether of (B1) a compound having a chain hydrocarbon moiety and 2-4 hydroxyl groups substituting hydrogens on the chain hydrocarbon moiety, and (B2) a compound having a chain hydrocarbon moiety and 1 hydroxyl group substituting a hydrogen on the chain hydrocarbon moiety;

(C) a complete ester of (C1) a carboxylic acid, alkoxy acid or oxoacid comprising a chain hydrocarbon moiety and 2-4 carboxyl groups substituting hydrogens on the chain hydrocarbon moiety, and (C2) a compound having a chain hydrocarbon moiety and 1 hydroxyl group substituting a hydrogen on the chain hydrocarbon moiety;

(D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety; and (E) a chain hydrocarbon.

As used herein, the term "complete ester" means a compound which is completely esterified, and the term "complete ether" means a compound which is completely etherified.

The compounds (A) to (E) will now be described in detail.

[(A) Complete Ester of (A1) a Compound Having a Chain Hydrocarbon Moiety and 2-4 Hydroxyl Groups Substituting Hydrogens on the Chain Hydrocarbon Moiety, and (A2) a Compound Having a Chain Hydrocarbon Moiety and 1 Carboxyl Group Substituting a Hydrogen on the Chain Hydrocarbon Moiety]

The (A) a complete ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety (hereunder also referred to as "compound (A)")

means a compound in which the hydroxyl groups of the (A1) compound having a chain hydrocarbon moiety and 2-4 hydroxyl groups substituting hydrogens on the chain hydrocarbon moiety (hereunder also referred to as "compound (A1)") are completely esterified with the (A2) compound having a chain hydrocarbon moiety and 1 carboxyl group substituting a hydrogen on the chain hydrocarbon moiety (hereunder also referred to as "compound (A2)").

Examples of compound (A1) include chain hydrocarbon tetraols, such as alkanetetraols, including pentaerythritol, chain hydrocarbon triols, such as alkanetriols, including glycerin, and chain hydrocarbon diols, such as alkanediols, including glycols. Examples of compound (A2) include compounds in which one hydrogen on the chain hydrocarbon moiety is substituted with one carboxyl group (—COOH), such as fatty acids.

Examples for compound (A) include ($a_1$) a tetraester of a chain hydrocarbon tetraol and same or different fatty acids, ($a_2$) a triester of a chain hydrocarbon triol and same or different fatty acids, and ($a_3$) a diester of a chain hydrocarbon diol and same or different fatty acids.

[($a_1$) Tetraester of a Chain Hydrocarbon Tetraol and Same or Different Fatty Acids]

Examples of ($a_1$) a tetraester of a chain hydrocarbon tetraol and same or different fatty acids include tetraesters of pentaerythritol and fatty acids, represented by the following formula (1):

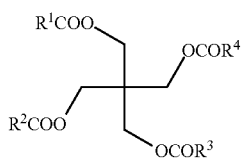

(1)

wherein $R^1$-$R^4$ each represent a chain hydrocarbon.

Examples of fatty acids in such tetraesters with pentaerythritols ($R^1$COOH, $R^2$COOH, $R^3$COOH, and $R^4$COOH) include saturated fatty acids, such as $C_2$-$C_{20}$ saturated fatty acids, including acetic acid ($C_2$) (the subscript numeral of "$C_2$" representing the number of carbons of each of $R^1$C, $R^2$C, $R^3$C or $R^4$C portion, same hereunder), propanoic acid ($C_3$), butanoic acid ($C_4$) and its isomers, such as 2-methylpropanoic acid ($C_4$), pentanoic acid ($C_5$) and its isomers, such as 2-methylbutanoic acid ($C_5$) and 2,2-dimethylpropanoic acid ($C_5$), hexanoic acid ($C_6$), heptanoic acid ($C_7$), octanoic acid ($C_8$) and its isomers, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$) and the like, as well as other isomers of the foregoing.

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{10}$), gadoleic acid ($C_{20}$) and eicosanoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and γ-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the tetraester of pentaerythritol and a fatty acid is preferably a tetraester of pentaerythritol and a fatty acid derived from a saturated fatty acid, or in other words, a tetraester of pentaerythritol and a saturated fatty acid.

In a tetraester of pentaerythritol and a fatty acid, the IOB is 0.34 if the total number of carbons of the fatty acid composing the tetraester of the pentaerythritol and fatty acid, i.e., the total number of carbons of the $R^1$C, $R^2$C, $R^3$C and $R^4$C portion in formula (1), is 30. Thus, when the total number of carbons of the fatty acid composing the tetraester of the pentaerythritol and fatty acid is about 30 or greater, the IOB satisfies the condition of being within about 0.00 to 0.35.

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_9$), decanoic acid ($C_{10}$) and/or dodecanoic acid ($C_{12}$).

Commercial products which are tetraesters of pentaerythritol and fatty acids include UNISTAR H-408BRS and H-2408BRS-22 (mixed product) (both products of NOF Corp.).

[($a_2$) Triester of a Chain Hydrocarbon Triol and Same or Different Fatty Acids]

Examples of ($a_2$) a triester of a chain hydrocarbon triol and same or different fatty acids include triesters of glycerin and fatty acids, represented by the following formula (2):

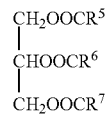

(2)

wherein $R^5$-$R^7$ each represent a chain hydrocarbon.

The fatty acid composing a triester of glycerin and a fatty acid ($R^5$COOH, $R^6$COOH and $R^7$COOH) may be one of the fatty acids, namely saturated fatty acids and unsaturated fatty acids, mentioned for "($a_1$) Tetraester of a chain hydrocarbon tetraol and same or different fatty acids", and in consideration of the potential for degradation by oxidation and the like, the triester is preferably a glycerin and fatty acid triester that is derived from a saturated fatty acid, or in other words, a triester of glycerin and a saturated fatty acid.

A triester of glycerin and a fatty acid is also known as a triglyceride, and examples include triesters of glycerin and octanoic acid (CO, triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid (CO and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

For a melting point of no higher than about 45° C., preferred triesters of glycerin and fatty acids are those with no more than about 40 as the total number of carbons of the fatty acid composing the triester of glycerin and the fatty, acid, i.e. the total number of carbons of the $R^5C$, $R^6C$ and $R^7C$ portions in formula (2).

In a triester of glycerin and a fatty acid, the IOB value is 0.35 when the total number of carbons of the fatty acid composing the triester of glycerin and the fatty acid, i.e. the total number of carbons of the $R^5C$, $R^6C$ and $R^7C$ portions in formula (2), is 23. Thus, when the total number of carbons of the fatty acid composing the triester of the glycerin and fatty acid is approximately 23 or greater, the IOB satisfies the condition of being within about 0.00 to 0.35.

Triesters of glycerin and fatty acids, being aliphatic and therefore potential constituent components of the human body, are therefore preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

[($a_3$) Diester of a Chain Hydrocarbon Diol and Same or Different Fatty Acids]

Examples of ($a_3$) a diester of a chain hydrocarbon diol and same or different fatty acids include diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specific examples of diesters of chain hydrocarbon diols and fatty acids include diesters of glycol and fatty acids, represented by the following formula (3):

$$R^8COOC_kH_{2k}OCOR^9 \quad (3)$$

wherein k is an integer of 2-6 and $R^8$ and $R^9$ each represent a chain hydrocarbon.

In a diester of glycol and a fatty acid, the fatty acid that is to be esterified (which corresponds to $R^8COOH$ or $R^9COOH$ in formula (3)) may be one of the fatty acids, namely saturated fatty acids or unsaturated fatty acids, mentioned for "($a_1$) Tetraester of a chain hydrocarbon tetraol and same or different fatty acids", and in consideration of the potential for degradation by oxidation and the like, it is preferably a saturated fatty acid.

In a diester of butylene glycol (k=4) and a fatty acid, represented by formula (3), IOB is 0.33 when the total number of carbons of the $R^8C$ and $R^9C$ portions is 14. Thus, when the total number of carbon atoms in a diester of butylene glycol (k=4) and a fatty acid represented by formula (3) is approximately 14 or greater, the IOB satisfies the condition of being about 0.00-0.35.

Considering the potential for degradation by oxidation and the like, the diester of glycol and a fatty acid is preferably a diester of glycol and a fatty acid derived from a saturated fatty acid, or in other words, a diester of glycol and a saturated fatty acid.

Also, in order to lower the IOB and result in greater hydrophobicity, the diester of the glycol and fatty acid is preferably a glycol and fatty acid diester derived from a glycol with a greater number of carbons, such as a diester of a glycol and a fatty acid derived from butylene glycol, pentylene glycol or hexylene glycol.

An example of a commercially available glycol and fatty acid diester is UNISTAR H-208BRS (product of NOF Corp.).

[(B) Complete Ether of (B1) a Compound Having a Chain Hydrocarbon Moiety and 2-4 Hydroxyl Groups Substituting Hydrogens on the Chain Hydrocarbon Moiety, and (B2) a Compound Having a Chain Hydrocarbon Moiety and 1 Hydroxyl Group Substituting a Hydrogen on the Chain Hydrocarbon Moiety]

The (B) complete ether of (B1) a compound having a chain hydrocarbon moiety and 2-4 hydroxyl groups substituting hydrogens on the chain hydrocarbon moiety, and (B2) a compound having a chain hydrocarbon moiety and 1 hydroxyl group substituting a hydrogen on the chain hydrocarbon moiety (hereunder also referred to as "compound (B)") means a compound in which the hydroxyl groups of the (B1) compound having a chain hydrocarbon moiety and 2-4 hydroxyl groups substituting hydrogens on the chain hydrocarbon moiety (hereunder also referred to as "compound (B1)") completely etherified with the (B2) compound having a chain hydrocarbon moiety and 1 hydroxyl group substituting a hydrogen on the chain hydrocarbon moiety (hereunder also referred to as "compound (B2)").

Examples of compound (B1) include those mentioned for "compound (A1)", such as pentaerythritol, glycerin and glycol.

Examples of compound (B2) include compounds wherein 1 hydrogen on the chain hydrocarbon moiety is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$), isopropyl alcohol ($C_3$), n-butyl alcohol ($C_4$), sec-butyl alcohol ($C_4$), tert-butyl alcohol ($C_4$), pentyl alcohol ($C_5$), hexyl alcohol ($C_6$), heptyl alcohol ($C_7$), octyl alcohol ($C_3$), 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers.

Unsaturated aliphatic monohydric alcohols include those wherein 1 C—C single bond of a saturated aliphatic monohydric alcohol mentioned above is replaced with a C═C double bond, such as oleyl alcohol, and for example, these are commercially available by New Japan Chemical Co., Ltd. as the RIKACOL Series and UNJECOL Series.

Examples for compound (B) include ($b_1$) a tetraether of a chain hydrocarbon tetraol and same or different aliphatic monohydric alcohols, ($b_2$) a triether of a chain hydrocarbon triol and same or different aliphatic monohydric alcohols and ($b_3$) a diether of a chain hydrocarbon diol and same or different aliphatic monohydric alcohols.

Examples of ($b_1$) a tetraether of a chain hydrocarbon tetraol and same or different aliphatic monohydric alcohols include tetraethers of pentaerythritol and aliphatic monohydric alcohols, represented by the following formula (4):

wherein $R^{10}$-$R^{13}$ each represent a chain hydrocarbon.

Examples of ($b_2$) a triether of a chain hydrocarbon triol and same or different aliphatic monohydric alcohols include triethers of glycerin and aliphatic monohydric alcohols, represented by the following formula (5):

(5)

wherein $R^{14}$-$R^{16}$ each represent a chain hydrocarbon.

Examples of ($b_3$) a diether of a chain hydrocarbon diols and same or different aliphatic monohydric alcohols include diethers of glycol and aliphatic monohydric alcohols, represented by the following formula (6):

$$R^{17}OC_nH_{2n}OR^{18} \qquad (6)$$

wherein n is an integer of 2-6, and $R^{17}$ and $R^{18}$ each represent a chain hydrocarbon.

In the tetraether of pentaerythritol and an aliphatic monohydric alcohol, the IOB is 0.33 when the total number of carbon atoms of the aliphatic monohydric alcohol composing the tetraether of pentaerythritol and the aliphatic monohydric alcohol, i.e. the total number of carbon atoms of the $R^{10}$, $R^{11}$, $R^{12}$ and $R^{13}$ portions in formula (4), is 7. Thus, when the total number of carbon atoms of the aliphatic monohydric alcohol composing a tetraether of pentaerythritol and an aliphatic monohydric alcohol is approximately 7 or greater, the IOB value satisfies the condition of being within about 0.00 to 0.35.

In the triether of glycerin and an aliphatic monohydric alcohol, the IOB is 0.33 when the total number of carbon atoms of the aliphatic monohydric alcohol composing the triether of glycerin and the aliphatic monohydric alcohol, i.e. the total number of carbon atoms of the $R^{14}$, $R^{15}$ and $R^{16}$ portions in formula (5), is 6. Thus, when the total number of carbon atoms of the aliphatic monohydric alcohol composing a triether of glycerin and an aliphatic monohydric alcohol is approximately 6 or greater, the IOB value satisfies the condition of being within about 0.00 to 0.35.

In a diether of butylene glycol (n=4) and an aliphatic monohydric alcohol represented by formula (6), the IOB is 0.33 when the total number of carbon atoms of the $R^{17}$ and $R^{18}$ portions is 2. Thus, when the number of carbon atoms of the aliphatic monohydric alcohol composing a diether of butylene glycol (n=4) and an aliphatic monohydric alcohol represented by formula (6) is approximately 2 or greater, the IOB value satisfies the condition of being within about 0.00 to 0.35.

The effects of double bonds, triple bonds, iso-branches and tert-branches are not considered in this calculation.

[(C) Complete Ester of (C1) a Carboxylic Acid, Alkoxy Acid or Oxoacid Comprising a Chain Hydrocarbon Moiety and 2-4 Carboxyl Groups Substituting Hydrogens on the Chain Hydrocarbon Moiety, and (C2) a Compound Having a Chain Hydrocarbon Moiety and 1 Hydroxyl Group Substituting a Hydrogen on the Chain Hydrocarbon Moiety]

The (C) complete ester of (C1) a carboxylic acid, alkoxy acid or oxoacid comprising a chain hydrocarbon moiety and 2-4 carboxyl groups substituting hydrogens on the chain hydrocarbon moiety, and (C2) a compound having a chain hydrocarbon moiety and 1 hydroxyl group substituting a hydrogen on the chain hydrocarbon moiety (hereunder also referred to as "compound (C)") means a compound in which the carboxyl groups of the (C1) carboxylic acid, alkoxy acid or oxoacid comprising a chain hydrocarbon moiety and 2-4 carboxyl groups substituting hydrogens on the chain hydrocarbon moiety (hereunder also referred to as "compound (C1)") are completely esterified with the (C2) compound having a chain hydrocarbon moiety and 1 hydroxyl group substituting a hydrogen on the chain hydrocarbon moiety (hereunder also referred to as "compound (C2)").

Examples of compound (C1) include chain hydrocarbon carboxylic acids with 2-4 carboxyl groups, such as chain hydrocarbon dicarboxylic acids including alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Examples of compound (C1) also include chain hydrocarbon alkoxy acids with 2-4 carboxyl groups, such as O-acetylcitric acid, and chain hydrocarbon oxoacids with 2-4 carboxyl groups.

Examples of compound (C2) include those mentioned for the "compound (B2)", such as aliphatic monohydric alcohols.

The compound (C) includes ($c_1$) a tetraester of a chain hydrocarbon tetracarboxylic acid, alkoxy acid or oxoacid with 4 carboxyl groups, and same or different aliphatic monohydric alcohols, ($c_2$) a triester of a chain hydrocarbon tricarboxylic acid, alkoxy acid or oxoacid with 3 carboxyl groups, and same or different aliphatic monohydric alcohols, and ($c_3$) a diester of a chain hydrocarbon dicarboxylic acid, alkoxy acid or oxoacid with 2 carboxyl groups, and same or different aliphatic monohydric alcohols.

Examples for compound (C) include dioctyl adipate and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") include ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Examples of ($D_1$) an ether of an aliphatic monohydric alcohol and an aliphatic monohydric alcohol include compounds having the following formula (7):

$$R^{19}OR^{20} \qquad (7)$$

wherein $R^{19}$ and $R^{20}$ each represent a chain hydrocarbon.

Examples for aliphatic monohydric alcohols in the ether (corresponding to $R^{19}OH$ and $R^{20}OH$ in formula (7)) include the aliphatic monohydric alcohols mentioned for the "compound (B2)".

In an ether of an aliphatic monohydric alcohol and an aliphatic monohydric alcohol, the IOB is 0.33 when the total number of carbons of the aliphatic monohydric alcohols of the ether, i.e. the total number of carbons of the $R^{19}$ and $R^{20}$ portions in formula (7), is 3, and therefore when the total number of carbons is about 3 or greater, the condition of the IOB being between about 0.00 and 0.35 is satisfied. However, a compound in which a total number of carbons of aliphatic monohydric alcohols of an ether is about 6, the water solubility thereof is as high as about 2 g, which is problematic from the viewpoint of vapor pressure as well. In order to satisfy the condition of a water solubility of about 0.00-0.05 g, the total number of carbons of the aliphatic monohydric alcohols of the ether is preferably about 8 or greater.

[($d_2$) Dialkyl Ketone]

The examples of ($d_2$) a dialkyl ketone comprise a compound having the following formula (8):

$$R^{21}COR^{22} \qquad (8)$$

wherein $R^{21}$ and $R^{22}$ are each an alkyl group.

In a dialkyl ketone, the IOB is 0.33 when the total number of carbon atoms of $R^{21}$ and $R^{22}$ is 9, and therefore the condition of the IOB being between about 0.00 and 0.35 is satisfied if the total number of carbons is about 9 or greater. The total number of carbon atoms in the dialkyl ketone is therefore preferably at least about 9.

The dialkyl ketone may be a commercially available product, or it may be obtained by a known method, such as by oxidation of a secondary alcohol with chromic acid or the like.

[($d_3$) Ester of a Fatty Acid and an Aliphatic Monohydric Alcohol]

Examples of ($d_3$) an ester of a fatty acid and an aliphatic monohydric alcohol include compounds having the following formula (9):

$$R^{23}COOR^{24} \qquad (9)$$

wherein $R^{23}$ and $R^{24}$ each represent a chain hydrocarbon.

Examples of fatty acids in these esters (corresponding to $R^{23}$COOH in formula (9)) include the fatty acids mentioned for the "($a_1$) tetraester of a chain hydrocarbon tetraol and same or different fatty acids", and specifically these include saturated fatty acids and unsaturated fatty acids, with saturated fatty acids being preferred in consideration of the potential for degradation by oxidation and the like. Examples for aliphatic monohydric alcohols in the ester (corresponding to $R^{24}$OH in formula (9)) include the aliphatic monohydric alcohols mentioned for the "compound (B2)".

In an ester of such a fatty acid and aliphatic monohydric alcohol, the IOB is 0.33 when the total number of carbon atoms of the fatty acid and aliphatic monohydric alcohol, i.e. the total number of carbon atoms of the $R^{23}$C and $R^{24}$ portions in formula (9), is 9. Therefore, in the ester of a fatty acid and an aliphatic monohydric alcohol, the condition of the IOB being between about 0.00 and 0.35 is satisfied if the total number of carbons of the $R^{23}$C and $R^{24}$ portions is about 9 or greater.

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($d_4$) Dialkyl Carbonate]

The examples of ($d_4$) a dialkyl carbonate comprise a compound of the following formula (10):

$$R^{25}OC(=O)OR^{26} \qquad (10)$$

wherein $R^{25}$ and $R^{26}$ are each an alkyl group.

In a dialkyl carbonate, the IOB is 0.33 when the total number of carbon atoms of $R^{25}$ and $R^{26}$ is 11, and therefore the condition of the IOB being between about 0.00 and 0.35 is satisfied if the total number of carbons of $R^{25}$ and $R^{26}$ is about 11 or greater.

The dialkyl carbonate may be a commercially available product, or it may be synthesized by reaction between phosgene and an alcohol, reaction between formic chloride and an alcohol or alcoholate, or reaction between silver carbonate and an alkyl iodide.

[(E) Chain Hydrocarbon]

The chain hydrocarbon has an inorganic value of 0 and thus an IOB of 0.00, while the water solubility is also approximately 0.00 g. Examples of (E) a chain hydrocarbon include ($e_1$) a chain alkane, such as linear alkanes and branched alkanes, and linear alkanes generally have a melting point of no higher than about 45° C. if their number of carbons is no greater than 22. In consideration of vapor pressure, they preferably have 13 or more carbons. Branched alkanes generally include those with 22 or more carbons, since their melting points are often higher than linear alkanes, given the same number of carbon atoms.

Examples of commercially available chain hydrocarbon products include PARLEAM 6 (NOF Corp.).

If the color-reducing agent has a melting point of no higher than about 45° C., it will liquefy (or will be a liquid) and will readily dissolve in a body fluid when it contacts with the body fluid at approximately 30-40° C., whether it is a liquid or solid at ordinary temperature (25° C.).

Also, a color-reducing agent having an IOB of between about 0.00 and 0.35 has high affinity with erythrocytes and can protect erythrocyte membranes, and therefore presumably helps prevent destruction of erythrocytes.

Any liquid-permeable top sheet that is commonly used or to be developed in the technical field may be employed without any particular restrictions, and for example, it may be a sheet-like material having a structure that allows permeation of liquids, such as a porous film, woven fabric, nonwoven fabric or the like. The fibers composing such a woven fabric or nonwoven fabric may be natural fibers or chemical fibers, with examples of natural fibers including cellulose such as ground pulp and cotton, and examples of chemical fibers including regenerated cellulose, such as rayon and fibril rayon, semi-synthetic cellulose, such as acetate and triacetate, thermoplastic hydrophobic chemical fibers, and hydrophilicized thermoplastic hydrophobic chemical fibers.

Examples of thermoplastic hydrophobic chemical fibers include polyethylene (PE), polypropylene (PP) and polyethylene terephthalate (PET) monofilaments, and fibers including PE and PP graft polymers.

Liquid-impermeable back sheets include films comprising PE and PP, air-permeable resin films, air-permeable resin films bonded to spunbond or spunlace nonwoven fabrics, and multilayer nonwoven fabrics, such as SMS. In consideration of flexibility of the absorbent article, a low-density polyethylene (LDPE) film with a basis weight of about 15-30 g/m², for example, is preferred.

The absorbent article in accordance with some embodiments of the disclosure comprises a second sheet between the liquid-permeable top sheet and the absorbent body. The second sheet may be any of the same examples as for the liquid-permeable top sheet.

A first example of the absorbent body is one having an absorbent core covered with a core wrap.

Examples of components for the absorption core include hydrophilic fibers, including cellulose, such as ground pulp or cotton, regenerated cellulose, such as rayon or fibril rayon, semi-synthetic cellulose, such as acetate or triacetate, particulate polymers, filamentous polymers, thermoplastic hydrophobic chemical fibers, and hydrophilicized thermoplastic hydrophobic chemical fibers, as well as combinations of the foregoing. The component of the absorbent core may also be a super absorbent polymer, such as granules of a sodium acrylate copolymer or the like.

The core wrap is not particularly restricted as long as it is a substance that is liquid-permeable and with a barrier property that does not allow permeation of the polymer absorber, and it may be a woven fabric or nonwoven fabric, for example. The woven fabric or nonwoven fabric may be made of a natural fiber, chemical fiber, tissue, or the like.

A second example of the absorbent body is one formed from an absorbing sheet or polymer sheet, with a thickness of preferably about 0.3-5.0 mm. The absorbing sheet or polymer sheet may usually be used without any particular restrictions as long as it is one that can be used in an absorbent article, such as a sanitary napkin.

When the liquid-permeable top sheet in the absorbent article described above comprises a color-reducing agent, the top sheet preferably contains the color-reducing agent on the skin contact surface (or the front side), and may further contain the color-reducing agent in its interior and/or on its absorbent body side (i.e., the back side or the skin-non-contact surface). If the color-reducing agent is present on the skin contact surface of the top sheet, menstrual blood will not easily remain on the skin contact surface of the top sheet. Also, when the color-reducing agent is present in the interior and/or on the absorbent body side of the top sheet, the color-reducing agent will not easily be shed and its effect will tend to last longer, even with excretion of sweat during use or with prolonged wear.

The color-reducing agent may be present at any location in the planar direction of the top sheet, such as across the entire top sheet, or at the center region to be disposed near the vaginal opening.

When the liquid-permeable top sheet is formed from a nonwoven fabric or woven fabric, the color-reducing agent preferably does not fill the voids between the fibers of the nonwoven fabric or woven fabric, and for example, the it may be attached as droplets or particulates on the surface of the nonwoven fabric fibers, or covering the surfaces of the fibers. On the other hand, when liquid-permeable top sheet is formed from a porous film, the color-reducing agent preferably does not fill the holes in the porous film, and for example, it may be attached as droplets or particulates on the surface of the porous film. This is because if the color-reducing agent fills the voids between the fibers of the nonwoven fabric or woven fabric or the holes in the porous film, migration of the absorbed liquid into the absorbent body may be inhibited.

The color-reducing agent also preferably has a large surface area, in order to allow rapid migration into the absorbed liquid, and a color-reducing agent present as droplets or particulates preferably has a small droplet/particle size.

When the absorbent article has a second sheet, the second sheet may also comprise a color-reducing agent. According to an embodiment of the absorbent article of the present disclosure, the absorbent body may also comprise a color-reducing agent.

In this type of absorbent article, the top sheet comprises the color-reducing agent at a basis weight in the range of preferably 1-30 g/m$^2$, more preferably 2-20 g/m$^2$ and more preferably 3-10 g/m$^2$. If the basis weight of the color-reducing agent is less than about 1 g/m$^2$ the color-reducing effect will tend to be insufficient, and if the basis weight of the color-reducing agent is increased, the stickiness during wearing will tend to be increased.

There are no particular restrictions on the method of coating the color-reducing agent, and coating may be accomplished with heating as necessary, using a non-contact coater, for example, a spiral coater, curtain coater, spray coater or dip coater, or a contact coater or the like. A non-contact coater is preferred from the viewpoint of uniformly dispersing the droplet or particulate color-reducing agent throughout, and from the viewpoint of not causing damage in the material. The color-reducing agent may be coated directly, if it is a liquid at room temperature, or it may be heated to lower the viscosity, and when it is a solid at room temperature, it may be heated to liquefaction, to a temperature of its melting point +20° C., for example, and coated using a control seam hot melt adhesive (HMA) gun. By increasing the air pressure of the control seam HMA gun, it is possible to coat the color-reducing agent as fine particulates.

The color-reducing agent may be coated during production of the top sheet material, such as the nonwoven fabric, or it may be coated in the manufacturing line for production of the absorbent article. From the viewpoint of minimizing equipment investment, the color-reducing agent is preferably coated in the manufacturing line for the absorbent article, and in order to prevent shedding of the color-reducing agent which may contaminate the line, it is preferably coated during a step downstream from the manufacturing line, and specifically, immediately before encapsulation of the product in an individual package.

When the material to be coated with the color-reducing agent, such as the top sheet, is a nonwoven fabric or porous film made of a synthetic resin, it is preferably coated with or mixed with a hydrophilic agent for hydrophilicizing treatment. If the original material is hydrophilic, since it is subsequently coated with a lipophilic color-reducing agent having an IOB of between about 0.00 and 0.35 and high organicity, there will be created sparsely dispersed lipophilic regions and hydrophilic regions. This presumably allows a consistent effect to be exhibited for menstrual blood which consists of hydrophilic components (blood plasma, etc.) and lipophilic components (blood cells, etc.).

The color-reducing agent preferably has a weight-average molecular weight of no greater than about 2,000, and more preferably no greater than about 1,000. This is because a high weight-average molecular weight will make it difficult to lower the viscosity of the color-reducing agent to an appropriate viscosity for coating, and may require dilution with a solvent. In addition, a high weight-average molecular weight will create tack in the color-reducing agent and may result in an unpleasant feeling for the wearer.

The absorbent article is preferably one intended for absorption of blood, such as a sanitary napkin, panty liner or the like.

With an absorbent article according to the disclosure, there is no need for components such as emollients and immobilizing agents, unlike absorbent articles containing a skin care composition, lotion composition or the like. In some embodiments, it is sufficient to apply to the top sheet the color-reducing agent alone.

EXAMPLES

Several examples will now be explained, with the understanding that the disclosure is not meant to be limited to the examples.

The following color-reducing agents were used for the test.

[(a₁) Tetraester of a Chain Hydrocarbon Tetraol and Same or Different Fatty Acids]
UNISTAR H-408BRS, product of NOF Corp.
Pentaerythritol tetra(2-ethylhexanoate)
UNISTAR H-2408BRS-22, product of NOF Corp.
Mixture of pentaerythritol tetra (2 ethylhexanoate) and neopentylglycol di(2-ethylhexanoate) (58:42 as mass ratio)
[(a₂) Triester of a Chain Hydrocarbon Triol and Same or Different Fatty Acids]
Cetiol SB45DEO, Cognis Japan
Glycerin and fatty acid triester, with oleic acid or stearylic acid as the fatty acid.
SOY42, product of NOF Corp.
Glycerin and fatty acid triester with $C_{14}$ fatty acid:$C_{16}$ fatty acid:$C_{18}$ fatty acid:$C_{20}$ fatty acid (including both saturated fatty acids and unsaturated fatty acids) at a mass ratio of about 0.2:11:88:0.8.
Tri-C2L oil fatty acid glyceride, product of NOF Corp.
Glycerin and fatty acid triester with $C_8$ fatty acid:$C_{10}$ fatty acid:$C_{12}$ fatty acid at a mass ratio of about 37:7:56.
Tri-CL oil fatty acid glyceride, product of NOF Corp.
Glycerin and fatty acid triester with $C_8$ fatty acid:$C_{12}$ fatty acid at a mass ratio of about 44:56.
PANACET 810s, product of NOF Corp.
Glycerin and fatty acid triester with $C_8$ fatty acid:$C_{10}$ fatty acid at a mass ratio of about 85:15.
PANACET 800, product of NOF Corp.
Glycerin and fatty acid triester with octanoic acid ($C_8$) as the entire fatty acid portion.
PANACET 800B, product of NOF Corp.
Glycerin and fatty acid triester with 2-ethylhexanoic acid ($C_8$) as the entire fatty acid portion.
NA36, product of NOF Corp.
Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3.
Tri-coconut fatty acid glyceride, product of NOF Corp.
Glycerin and fatty acid triester with $C_8$ fatty acid: $C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3.
[(a₃) Diester of a Chain Hydrocarbon Diol and Same or Different Fatty Acids]
UNISTAR H-208BRS, product of NOF Corp.
Neopentylglycol di(2-ethylhexanoate)
[(c₃) Diester of a Chain Hydrocarbon Dicarboxylic Acid, Alkoxy Acid or Oxoacid with 2 Carboxyl Groups, and Same or Different Aliphatic Monohydric Alcohols]
Dioctyl adipate, product of Wako Pure Chemical Industries, Ltd.
[(d₃) Ester of a Fatty Acid and an Aliphatic Monohydric Alcohol]
ELECTOL WE20, product of NOF Corp.
Ester of dodecanoic acid ($C_{12}$) and dodecyl alcohol ($C_{12}$)
ELECTOL WE40, product of NOF Corp.
Ester of tetradecanoic acid ($C_{14}$) and dodecyl alcohol ($C_{12}$)
[(e₁) Chain Alkane]
PARLEAM 6, product of NOF Corp.
Branched hydrocarbon, produced by copolymerization of liquid isoparaffin, isobutene and n-butene followed by hydrogen addition, polymerization degree: approximately 5-10.
[Other Components]
NA50, product of NOF Corp.
Glycerin and fatty acid triester obtained by addition of hydrogen to NA36 for reduced proportion of double bonds from unsaturated fatty acid starting material.
Caprylic acid diglyceride, product of NOF Corp.
Glycerin and fatty acid diester with octanoic acid as the fatty acid.
(Caprylic acid/capric acid) monoglyceride, product of NOF Corp.
Glycerin and fatty acid monoester, with octanoic acid ($C_8$) and decanoic acid ($C_{10}$) at a mass ratio of about 85:15.
Monomuls 90-L2 lauric acid monoglyceride, product of Cognis Japan
UNIOX HC60, product of NOF Corp.
Polyoxyethylene hydrogenated castor oil
WILBRITE s753, product of NOF Corp.
Polyoxyethylene-polyoxypropylene-polyoxybutylene glycerin
Tributyl citrate, product of Tokyo Kasei Kogyo Co., Ltd.
Isopropyl citrate, product of Tokyo Kasei Kogyo Co., Ltd.
COMPOL BL, product of NOF Corp.
Dodecanoic acid ($C_{12}$) monoester of butylene glycol
COMPOL BS, product of NOF Corp.
Octadecanoic acid ($C_{18}$) monoester of butylene glycol
UNIOL D-400 (All UNIOLs are products of NOF Corp.)
Polypropylene glycol, weight-average molecular weight: approximately 400
UNIOL D-1000
Polypropylene glycol, weight-average molecular weight: approximately 1,000
UNIOL D-1200
Polypropylene glycol, weight-average molecular weight: approximately 1,200
UNIOL D-3000
Polypropylene glycol, weight-average molecular weight: approximately 3,000
UNIOL D-4000
Polypropylene glycol, weight-average molecular weight: approximately 4,000
UNIOL PB500
Polybutylene glycol, weight-average molecular weight: approximately 500
UNIOL PB700
Polybutylene glycol, weight-average molecular weight: approximately 700
UNIOL PB1000R
Polybutylene glycol, weight-average molecular weight: approximately 1,000
WILBRITE cp9, product of NOF Corp.
Polybutylene glycol compound with OH groups at both ends esterified by hexadecanoic acid ($C_{16}$), weight-average molecular weight: approximately 1100
UNILUBE MS-70K, product of NOF Corp.
Stearyl ether of polypropylene glycol, approximately 15 repeating units
PEG1500, product of NOF Corp.
Polyethylene glycol, weight-average molecular weight: approximately 1500-1600
Vaseline, product of Cognis Japan
Petroleum-derived hydrocarbon, semi-solid
NONION S-6, product of NOF Corp.
Polyoxyethylene monostearate, approximately 7 repeating units, weight-average molecular weight: approximately 600
UNIOL TG-330, product of NOF Corp.
Glyceryl ether of polypropylene glycol, approximately 6 repeating units, weight-average molecular weight: approximately 330
UNIOL TG-1000, product of NOF Corp.
Glyceryl ether of polypropylene glycol, approximately 16 repeating units, weight-average molecular weight: approximately 1,000
UNILUBE DGP-700, product of NOF Corp.

Diglyceryl ether of polypropylene glycol, approximately 9 repeating units, weight-average molecular weight: approximately 700

Production Example 1

A commercially available sanitary napkin was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150-450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The skin contact surface of the top sheet of the sanitary napkin was coated with H-408BRS. Specifically, H-408BRS was atomized using a control seam HMA gun and coated over the entire skin contact surface of the top sheet to a basis weight of about 5 g/m$^2$, to prepare sanitary napkin No. 1-1.

Production Examples 2-6

Sanitary napkin Nos. 1-2 to 1-6 were prepared in the same manner as Production Example 1, except that H-408BRS was changed to the compounds listed in Table 2, and tri C2L oil fatty acid glyceride having a melting point of 37° C., and WE40, were heated to about 57° C. before coating.

Comparative Production Examples 1-7

Sanitary napkin Nos. 1-7 to 1-13 were prepared in the same manner as Production Example 1, except that H-408BRS was changed to the compounds listed in Table 2, and the compound was heated to its melting point +20° C. as necessary before coating.

Comparative Production Example 9

The untreated commercially available sanitary napkin used in Production Example 1 was used as sanitary napkin No. 1-14.

Example 1

Sanitary napkin Nos. 1-1 to 1-14 were subjected to a liquid residue test and a liquid dropping test by the methods described above. The absorbance in the liquid residue test was measured using a microplate reader (Model EL808IU) by Bio-Tek Instruments, Inc, and the color difference in the liquid dropping test was measured using a Chroma Meter CR-300 by Konica Minolta Holdings, Inc. Table 2 shows the absorbances, color differences and blood cell counts per 1 g of top sheet.

The horse EDTA blood used was 65 mL of horse venous blood, with addition of 0.5 mL of 12% EDTA·2K physiological saline.

Figure 2:
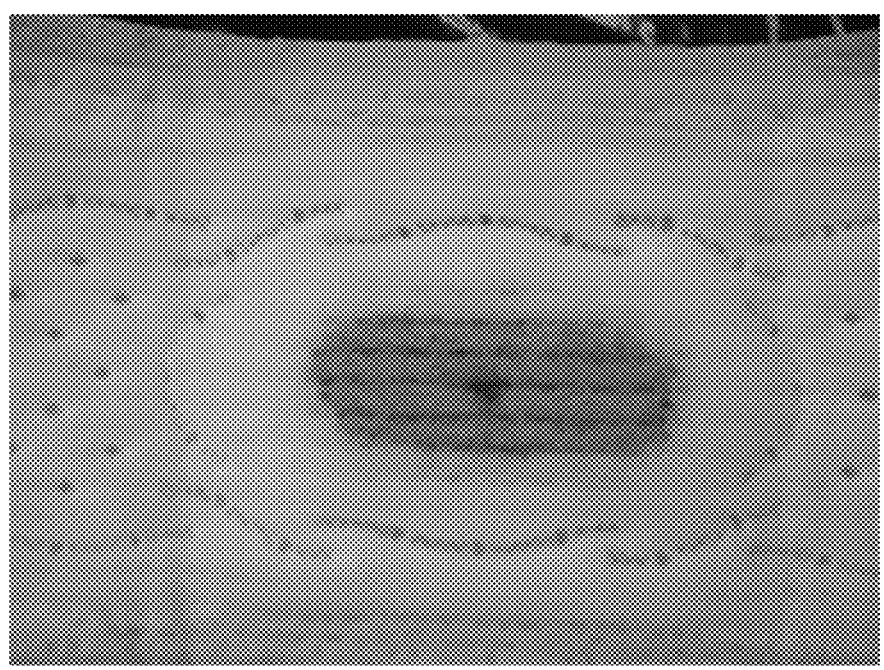
FIG. 2 is an image of sanitary napkin No. 1-2, under the same conditions.
Figure 3:
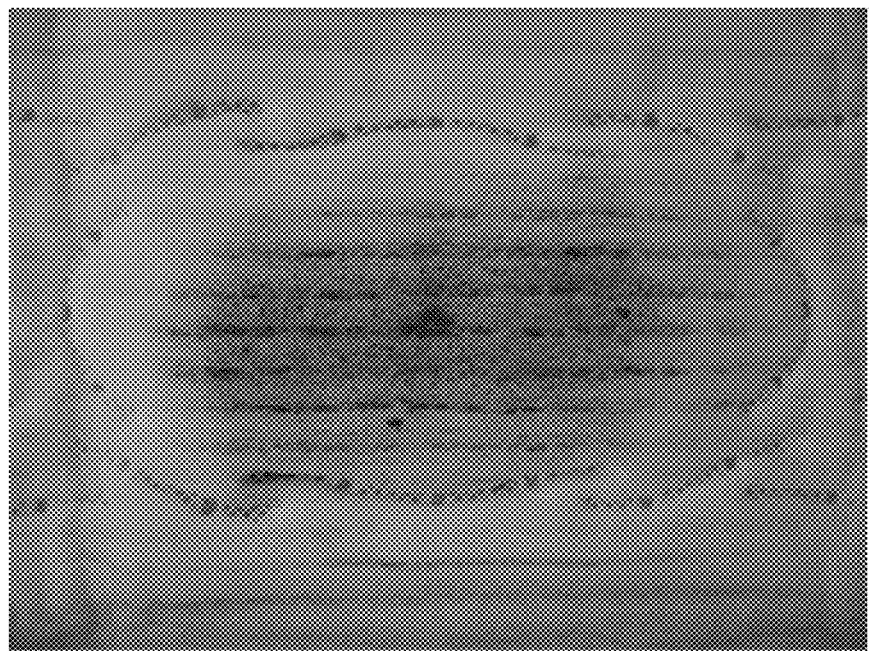
FIG. 3 is an image of sanitary napkin No. 1-4, under the same conditions.
Figure 4:
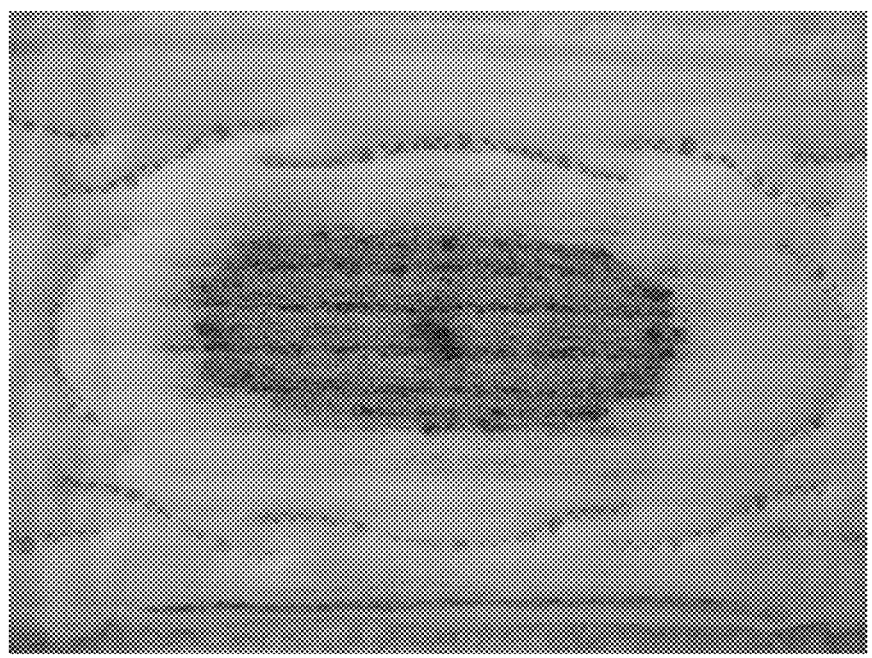
FIG. 4 is an image of sanitary napkin No. 1-5, under the same conditions.
Figure 5:
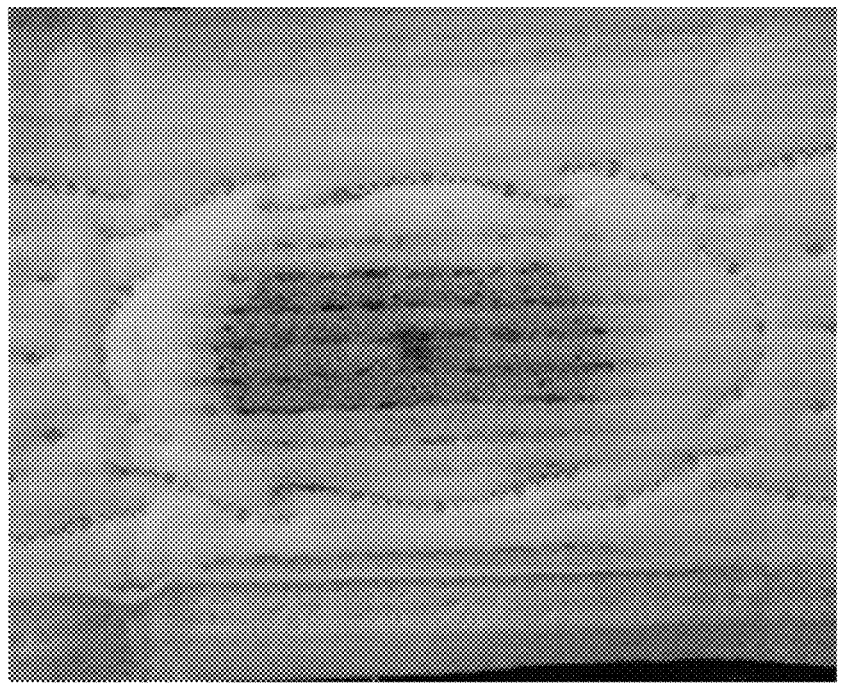
FIG. 5 is an image of sanitary napkin No. 1-6, under the same conditions.
Figure 6:
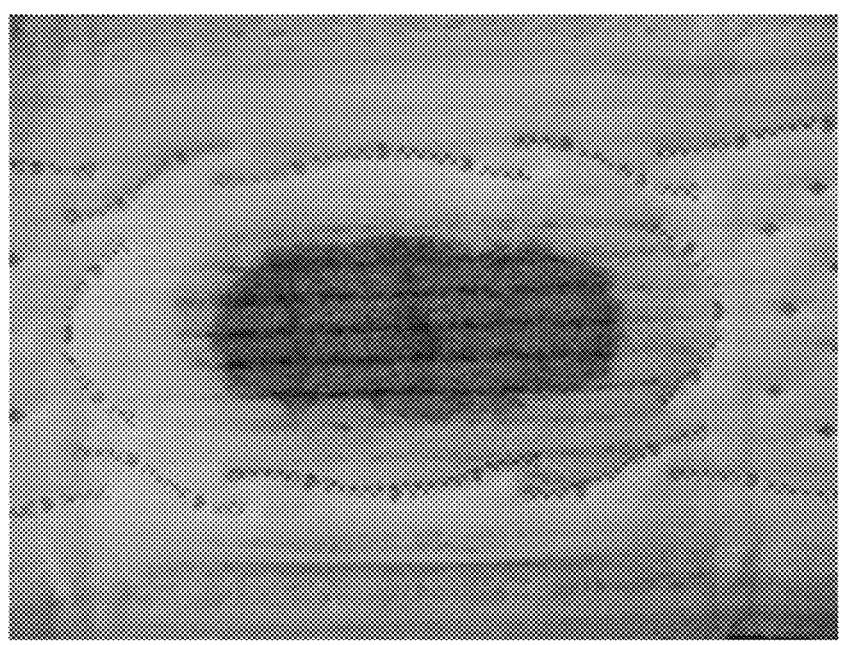
FIG. 6 is an image of sanitary napkin No. 1-7, under the same conditions.
Figure 7:
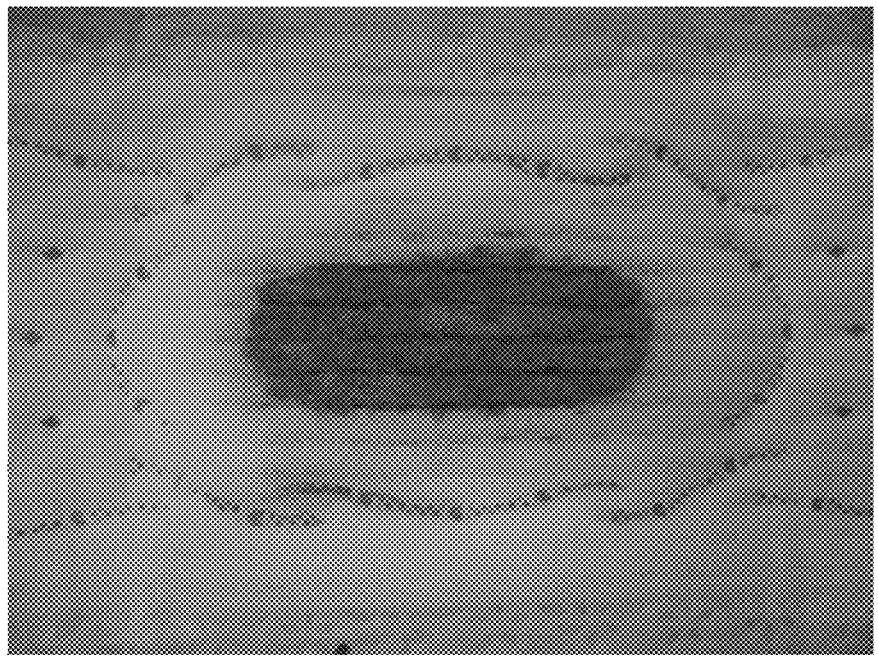
FIG. 7 is an image of sanitary napkin No. 1-9, under the same conditions.
Figure 8:
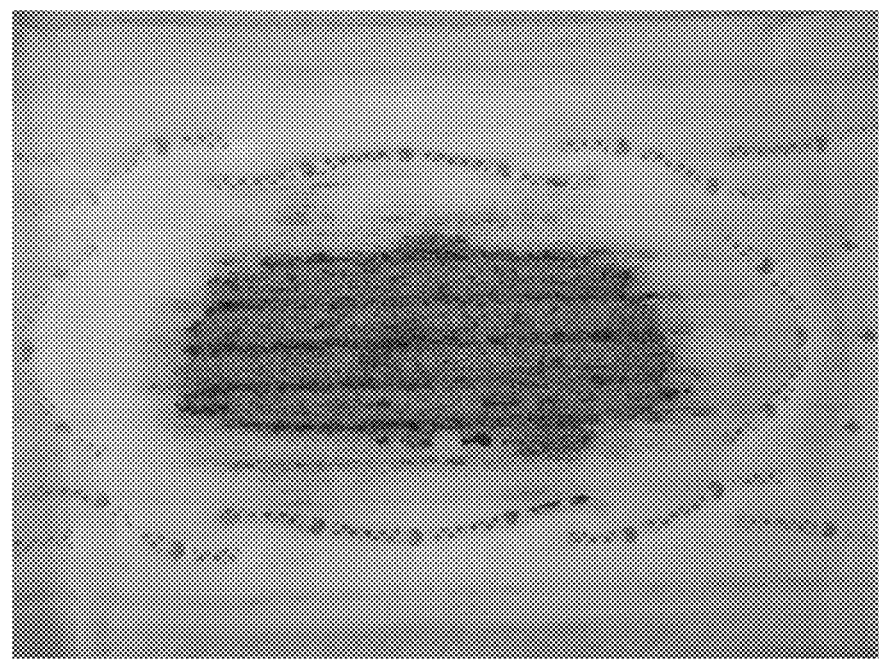
FIG. 8 is an image of sanitary napkin No. 1-10, under the same conditions.
Figure 9:
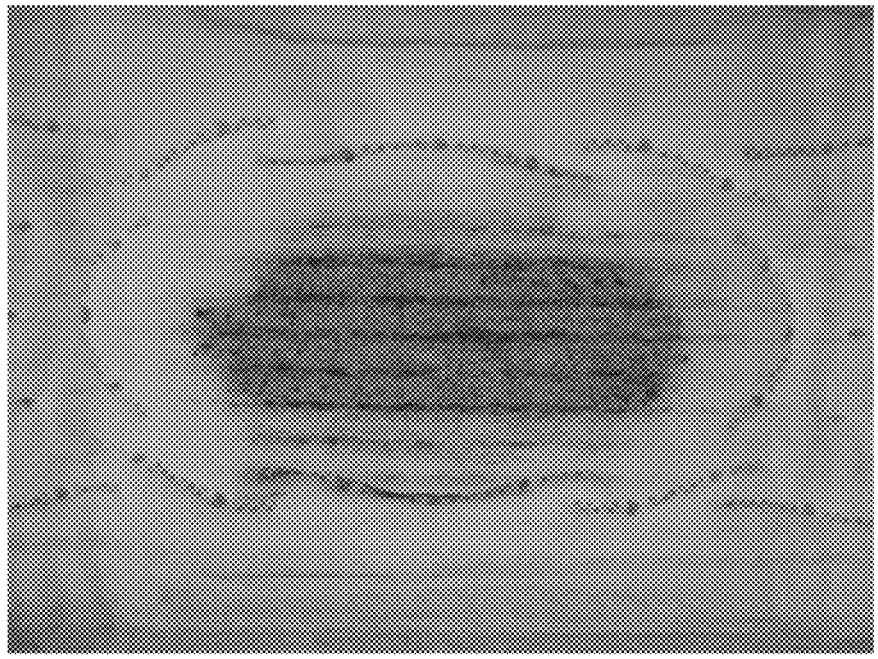
FIG. 9 is an image of sanitary napkin No. 1-11, under the same conditions.
Figure 10:
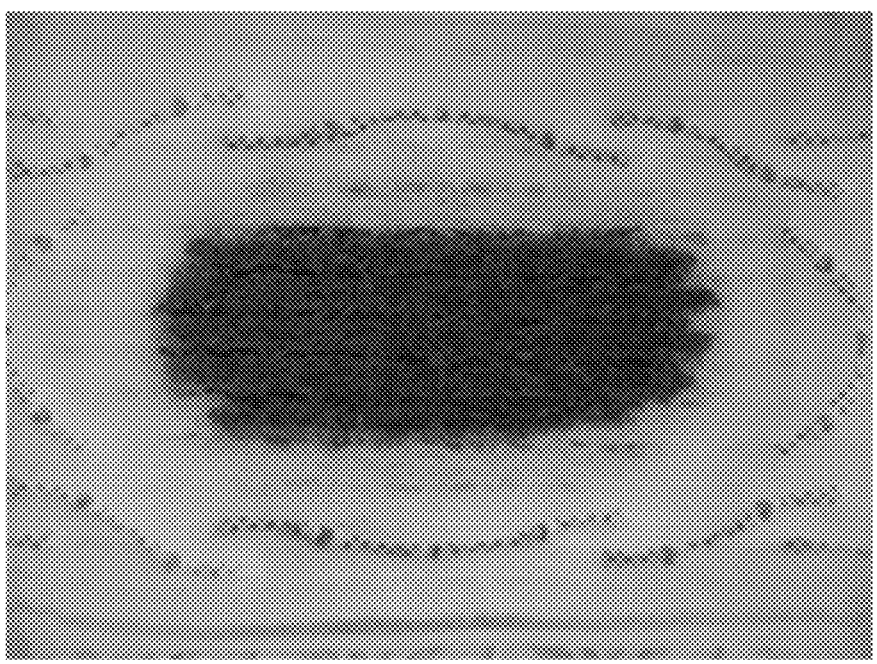
FIG. 10 is an image of sanitary napkin No. 1-14, under the same conditions.

FIGS. 1 to 5 show images of sanitary napkin Nos. 1-1, 1-2, 1-4, 1-5 and 1-6, 40 seconds after completion of the second horse EDTA blood dropping in the liquid residue test. FIGS. 6 to 10 show similar images of sanitary napkin Nos. 1-7, 1-9, 1-10, 1-11 and 1-14.

The rewetting rates and absorbent body migration rates of sanitary napkin Nos. 1-1 to 1-14 were measured next.

The rewetting rate was determined by conducting procedures (1) and (2) of the liquid dropping test described above, and then immediately removing the acrylic board and placing 10 filter paper sheets (50 mm×35 mm) with pre-measured mass on the horse EDTA blood-dropped area, setting a weight thereover to a pressure of 30 g/cm$^2$, and after 1 minute, removing the filter paper and measuring its mass including the horse EDTA blood, and performing the following calculation.

Rewetting rate(%)=100×(filter paper mass after test−initial filter paper mass)/6

The absorbent body migration rate was evaluated by conducting procedures (1) and (2) of the liquid dropping test described above, and measuring the time from procedure (2) until the horse EDTA blood migrated from the top sheet into the absorbent body.

The results for the rewetting rate and absorbent body migration rate are summarized below in Table 2.

The data for the IOB values, melting points and water solubilities of the compounds listed in Table 2 are also shown in Table 2.

The water solubility was measured by the method described above, and samples that dissolved 24 hours after addition of 20.0 g to 100 g of desalted water were evaluated as "20<".

For the melting point, "<45" indicates a melting point below 45° C.

TABLE 2

| Sanitary napkin No. | Color-reducing agent | IOB | Melting point (° C.) | Water solubility (g) | Color difference ΔE | Absorbance | Blood cell count (×10$^7$/g) | Rewetting rate (%) | Absorbent body migration rate (sec) |
|---|---|---|---|---|---|---|---|---|---|
| 1-1 | H-408BRS | 0.13 | <−5 | <0.05 | 45.5 | 0.081 | 18 | 1.2 | 3 |
| 1-2 | Tri-C2L oil fatty acid glyceride | 0.27 | 37 | <0.05 | 44.1 | 0.071 | 5 | 0.3 | 3 |
| 1-3 | PANACET 810S | 0.32 | −5 | <0.05 | 47.8 | 0.061 | 26 | 2.8 | 3 |
| 1-4 | H-208BRS | 0.24 | <−5 | <0.05 | 39.4 | 0.070 | 15 | 2.0 | 5 |
| 1-5 | WE40 | 0.12 | 37 | <0.05 | 43.5 | 0.082 | 6 | 1.8 | 4 |
| 1-6 | PARLEAM 6 | 0.00 | −5 | <0.05 | 39.4 | — | — | 6.0 | 8 |
| 1-7 | Monomuls 90-L12 Lauric acid monoglyceride | 0.87 | 58 | <0.05 | 29.8 | 0.382 | 7 | 6.2 | 7 |
| 1-8 | COMPOL BL | 0.50 | 2 | <0.05 | 32.1 | 0.355 | 2 | 2.0 | 5 |
| 1-9 | NONION S-6 | 0.44 | 37 | 0.05< | 28.5 | — | — | 8.4 | 7 |
| 1-10 | UNIOL D-400 | 0.76 | <45 | 0.05< | 35.0 | 0.067 | 115 | 8.7 | 40 |
| 1-11 | UNIOL D-1000 | 0.51 | <45 | <0.05 | 35.3 | 0.064 | 65 | 6.8 | 15 |

TABLE 2-continued

| Sanitary napkin No. | Color-reducing agent | IOB | Melting point (° C.) | Water solubility (g) | Color difference ΔE | Absorbance | Blood cell count (×10$^7$/g) | Rewetting rate (%) | Absorbent body migration rate (sec) |
|---|---|---|---|---|---|---|---|---|---|
| 1-12 | UNIOL D-3000 | 0.39 | <45 | <0.05 | 35.2 | 0.065 | 94 | 1.7 | 10 |
| 1-13 | UNIOL D-4000 | 0.38 | <45 | <0.05 | 36.1 | 0.080 | 32 | 1.0 | 7 |
| 1-14 | — | — | — | — | 27.8 | 0.111 | 107 | 22.7 | 60< |

Table 2 shows that sanitary napkin Nos. 1-1 to 1-6 had more excellent rewetting rates and absorbent body migration rates than sanitary napkin No. 1-14.

Sanitary napkin Nos. 1-1, 1-2, 1-4, 1-5 and 1-6, which had color difference ΔE values in the range of 37-80, had almost no residue of horse EDTA blood on the top sheet and exhibited absorption of horse EDTA blood by the absorbent body, as can be clearly discerned from FIGS. 1 to 5.

Thus, sanitary napkin Nos. 1-1 to 1-6 which had color difference ΔE values in the range of 37-80 had excellent rewetting rates and absorbent body migration rates, with rapid migration of highly viscous menstrual blood into the absorbent body upon its absorption, while allowing the user to visually confirm low residue of menstrual blood on the top sheet, and they can therefore provide the user with a feeling of reassurance.

With Monomuls 90 L12 lauric acid monoglyceride, a large number of ruptured blood cell fragments were observed upon measuring the blood cell count. This matches the results of high absorbance (high hemoglobin content) for the low blood cell count.

Next, several volunteer subjects were asked to wear sanitary napkins Nos. 1-1 to 1-14, and the obtained responses indicated that sanitary napkin Nos. 1-1 to 1-6 allowed visual confirmation that no menstrual blood remained on the surface of the top sheet and that menstrual blood had migrated to the absorbent body, thus providing a better feeling of reassurance, compared to sanitary napkin Nos. 1-7 to 1-14. The responses also indicated that compared to sanitary napkin No. 1-14 as well, sanitary napkin Nos. 1-1 to 1-6 had more excellent absorption of menstrual blood and a more excellent feeling of smoothness even after absorption of menstrual blood.

Example 2

The compounds listed in Table 3 were coated on the commercially available sanitary napkin by the same procedure as Production Example 1 and evaluated for rewetting rate and absorbent body migration rate. The whiteness of the skin contact surface of the top sheet after the absorbent body migration rate test was visually evaluated on the following scale.

VG (Very Good): Virtually no redness of blood remaining, and no clear delineation between areas with and without blood.

G (Good): Slight redness of blood remaining, but difficult to delineate between areas with and without blood.

F (Fair): Slight redness of blood remaining, areas with blood discernible.

P (Poor): Redness of blood completely remaining.

The results are summarized below in Table 3.

TABLE 3

| No. | | Color-reducing agent | IOB | Melting point (° C.) | Water solubility (g) | Rewetting rate (%) | Absorbent body migration rate (sec) | Top sheet whiteness |
|---|---|---|---|---|---|---|---|---|
| 2-1 | (a$_1$) | H-408BRS | 0.13 | <−5 | <0.05 | 1.2 | 3 | VG |
| 2-2 | | H-2408BRS-22 | 0.18 | <−5 | <0.05 | 2.0 | 3 | VG |
| 2-3 | (a$_2$) | Cetiol SB45DEO | 0.16 | 44 | <0.05 | 7.0 | 6 | VG |
| 2-4 | | SOY42 | 0.16 | 43 | <0.05 | 5.8 | 8 | VG |
| 2-5 | | Tri-C2L oil fatty acid glyceride | 0.27 | 37 | <0.05 | 0.3 | 3 | VG |
| 2-6 | | Tri-CL oil fatty acid glyceride | 0.28 | 38 | <0.05 | 1.7 | 3 | VG |
| 2-7 | | PANACET 810s | 0.32 | −5 | <0.05 | 2.8 | 3 | VG |
| 2-8 | | PANACET 800 | 0.33 | −5 | <0.05 | 0.3 | 3 | VG |
| 2-9 | | PANACET 800B | 0.33 | −5 | <0.05 | 2.0 | 3 | VG |
| 2-10 | | NA36 | 0.16 | 37 | <0.05 | 3.9 | 5 | VG |
| 2-11 | | Tri-coconut oil fatty acid glyceride | 0.28 | 30 | <0.05 | 4.3 | 5 | VG |
| 2-12 | (a$_3$) | H-208BRS | 0.24 | <−5 | <0.05 | 2.0 | 5 | VG |
| 2-13 | (c$_3$) | Dioctyl adipate | 0.27 | <45 | <0.05 | 1.7 | 6 | VG |
| 2-14 | (d$_3$) | ELECTOL WE20 | 0.13 | 29 | <0.05 | 1.8 | 5 | VG |
| 2-15 | | ELECTOL WE40 | 0.12 | 37 | <0.05 | 1.8 | 4 | VG |
| 2-16 | (e$_1$) | PARLEAM 6 | 0.00 | −5 | <0.05 | 6.0 | 8 | VG |
| 2-17 | | NA50 | 0.18 | 52 | <0.05 | 15.5 | 60 | P |
| 2-18 | | Caprylic acid diglyceride | 0.58 | <45 | <0.05 | 4.2 | 9 | G |
| 2-19 | | (Caprylic acid/capric acid) monoglyceride | 1.15 | <45 | 20< | 4.0 | 4 | P |
| 2-20 | | 90-L2 Lauric acid monoglyceride | 0.87 | 58 | 20< | 6.2 | 7 | P |
| 2-21 | | UNIOX HC60 | 0.46 | 33 | 0.05-1.00 | 14.6 | 46 | P |
| 2-22 | | WILBRITE s753 | 0.67 | −5 | 20< | 9.3 | 9 | F |
| 2-23 | | Tributyl citrate | | | | | | |
| 2-24 | | Isopropyl citrate | 1.56 | <45 | 20< | 12.2 | 5 | G |
| 2-25 | | COMPOL BL | 0.50 | 2 | <0.05 | 2.0 | 5 | G |
| 2-26 | | COMPOL BS | 0.36 | 37 | <0.05 | 7.9 | 9 | G |
| 2-27 | | UNIOL D-400 | 0.76 | <45 | 0.05< | 8.7 | 40 | P |

TABLE 3-continued

| No. | Color-reducing agent | IOB | Melting point (° C.) | Water solubility (g) | Rewetting rate (%) | Absorbent body migration rate (sec) | Top sheet whiteness |
|---|---|---|---|---|---|---|---|
| 2-28 | UNIOL D-1000 | 0.51 | <45 | <0.05 | 6.8 | 15 | F |
| 2-29 | UNIOL D-1200 | 0.48 | <45 | <0.05 | 0.5 | 11 | F |
| 2-30 | UNIOL D-3000 | 0.39 | <45 | <0.05 | 1.7 | 10 | F |
| 2-31 | UNIOL D-4000 | 0.38 | <45 | <0.05 | 1.0 | 7 | G |
| 2-32 | UNIOL PB500 | 0.44 | <45 | <0.05 | 4.5 | 4 | G |
| 2-33 | UNIOL PB700 | 0.49 | −5 | <0.05 | 2.8 | 5 | G |
| 2-34 | UNIOL PB1000R | 0.40 | <45 | <0.05 | 4.0 | 4 | G |
| 2-35 | WILBRITE cp9 | 0.21 | 35 | <0.05 | 1.4 | 3 | G |
| 2-36 | UNILUBE MS-70K | 0.30 | <−10 | <0.05 | 6.7 | 3 | G |
| 2-37 | PEG1500 | 0.78 | 40 | 20< | 11.0 | 38 | P |
| 2-38 | Vaseline | 0.00 | 55 | <0.05 | 9.7 | 10 | F |
| 2-39 | NONION S-6 | 0.44 | 37 | 0.05< | 8.4 | 7 | P |
| 2-40 | UNIOL TG-330 | 1.27 | <45 | 0.05< | — | — | — |
| 2-41 | UNIOL TG-1000 | 0.61 | <45 | <0.05 | 14.2 | 7.3 | G |
| 2-42 | UNIOL DGP-700 | 0.90 | <0 | 0.05< | — | — | — |
| 2-43 | None | — | — | — | 22.7 | 60< | P |

The present disclosure relates to the following (J1) to (J10).

(J1)

An absorbent article comprising a liquid-permeable top sheet, a liquid-impermeable back sheet, and an absorbent body between the liquid-permeable top sheet and liquid-impermeable back sheet, wherein the top sheet exhibits a color difference in the range of 37-80, based on the L*a*b* color system and measured from a skin contact surface of the top sheet in a liquid dropping test.

(J2)

The absorbent article according to J1, wherein the top sheet has, in a liquid residue test, a hemoglobin content represented by absorbance of 0.00-0.10, and a blood cell count of 0-30× $10^7$/g.

(J3)

The absorbent article according to J1 or J2, wherein the top sheet comprises a color-reducing agent having an IOB of 0.00-0.35 and a melting point of no higher than 45° C.

(J4)

The absorbent article according to J3, wherein the color-reducing agent also has a water solubility of 0.00-0.05 g in 100 g of water at 25° C.

(J5)

The absorbent article according to J3 or J4, wherein the color-reducing agent is selected from the group consisting of following items (i) and (ii), and any combination thereof:

(i) a hydrocarbon; and (ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety, with the proviso that when 2 or more oxy groups (—O—) are inserted between the compound of (ii), the oxy groups are not adjacent to each other.

(J6)

The absorbent article according to any one of J3 to J5, wherein the color-reducing agent is selected from the group consisting of following items (i') and (ii'), and any combination thereof:

(i') a hydrocarbon; and (ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, with the proviso that when 2 or more same or different bonds are inserted between the compound of (ii'), the bonds are not adjacent to each other.

(J7)

The absorbent article according to any one of J3 to J6, wherein the color-reducing agent is selected from the group consisting of following items (A)-(E), and any combination thereof:

(A) a complete ester of (A1) a compound having a chain hydrocarbon moiety and (A2) 2-4 hydroxyl groups substituting hydrogens on the chain hydrocarbon moiety, and a compound having a chain hydrocarbon moiety and 1 carboxyl group substituting a hydrogen on the chain hydrocarbon moiety;

(B) a complete ether of (B1) a compound having a chain hydrocarbon moiety and 2-4 hydroxyl groups substituting hydrogens on the chain hydrocarbon moiety, and (B2) a compound having a chain hydrocarbon moiety and 1 hydroxyl group substituting a hydrogen on the chain hydrocarbon moiety;

(C) a complete ester of (C1) a carboxylic acid, alkoxy acid or oxoacid comprising a chain hydrocarbon moiety and 2-4 carboxyl groups substituting hydrogens on the chain hydrocarbon moiety, and (C2) a compound having a chain hydrocarbon moiety and 1 hydroxyl group substituting a hydrogen on the chain hydrocarbon moiety;

(D) a compound having a chain hydrocarbon moiety and one bond selected from the group consisting of an ether bond (—O—), carbonyl bond (—CO—), ester bond (—COO—) or carbonate bond (—OCOO—) inserted between a C—C single bond of the chain hydrocarbon moiety; and (E) a chain hydrocarbon.

(J8)

An absorbent article according to any one of J3 to J7, wherein the color-reducing agent is selected from the group consisting of ($a_1$) a tetraester of a chain hydrocarbon tetraol and same or different fatty acids, ($a_2$) a triester of a chain hydrocarbon triol and same or different fatty acids, ($a_3$) a diester of a chain hydrocarbon diol and same or different fatty acids, ($b_1$) a tetraether of a chain hydrocarbon tetraol and same or different aliphatic monohydric alcohols, ($b_2$) a triether of a chain hydrocarbon triol and same or different aliphatic monohydric alcohols, ($b_3$) a diether of a chain hydrocarbon diol and same or different aliphatic monohydric alcohols, ($c_1$) a tetraester of a chain hydrocarbon tetracarboxylic acid, alkoxy acid or oxoacid with 4 carboxyl groups and same or different aliphatic monohydric alcohols, ($c_2$) a triester of a chain hydrocarbon tricarboxylic acid, alkoxy acid or oxoacid with 3 carboxyl groups and same or different aliphatic monohydric alcohols, ($c_3$) a diester of a chain hydrocarbon dicarboxylic acid, alkoxy acid or oxoacid with 2 carboxyl groups and same or different aliphatic monohydric alcohols, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate and ($e_1$) linear alkane, and any combination thereof.

(J9)

The absorbent article according to any one of J3 to J8, wherein the color-reducing agent has the vapor pressure of 0.00-0.01 Pa at 1 atmosphere, 20° C. or 40° C.

(J10)

The absorbent article according to any one of J3 to J9, wherein the color-reducing agent has a weight-average molecular weight of no greater than 2,000.

(J11)

The absorbent article according to any one of J3 to J10, wherein the top sheet is formed from a nonwoven fabric or woven fabric, and the color-reducing agent is attached to the surfaces of the fibers of the nonwoven fabric or woven fabric.

(J12)

The absorbent article according to any one of J1 to J11, which is a sanitary napkin or panty liner.

In addition, the present disclosure relates to the following (E1) to (E15).

(E1)

An absorbent article comprising a liquid-permeable top sheet, a liquid-impermeable back sheet, and an absorbent body between the liquid-permeable top sheet and liquid-impermeable back sheet;

wherein the total color difference ΔE of the absorbent article is in the range of 37-80, based on the CIE L*a*b* color system and as measured from a skin contact surface of the top sheet in a liquid dropping test.

(E2)

The absorbent article according to E1, wherein the top sheet has, in a liquid residue test, a hemoglobin content represented by absorbance of 0.00-0.10.

(E3)

The absorbent article according to E1 or E2, wherein the top sheet has, in a liquid residue test, a blood cell count of $0\text{-}30\times10^7$/g.

(E4)

The absorbent article according to any one of E1 to E3, wherein the top sheet comprises a color-reducing agent having an IOB of 0.00-0.35 and a melting point of no higher than 45° C.

(E5)

The absorbent article according to E4, wherein the color-reducing agent has a water solubility of 0.00-0.05 g in 100 g of water at 25° C.

(E6)

The absorbent article according to E4 or E5, wherein the color-reducing agent has a vapor pressure of 0.00-0.01 Pa at 1 atmosphere and 25° C. or 40° C.

(E7)

The absorbent article according to any one of E4 to E6, wherein the color-reducing agent is selected from the group consisting of following items (i) and (ii), and any combination thereof:

(i) a hydrocarbon; and (ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety, with the proviso that when 2 or more oxy groups (—O—) are inserted between the compound of (ii), the oxy groups are not adjacent to each other.

(E8)

The absorbent article according to any one of E4 to E7, wherein the color-reducing agent is selected from the group consisting of following items (i') and (ii'), and any combination thereof:

(i') a hydrocarbon; and (ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, with the proviso that when 2 or more same or different bonds are inserted between the compound of (ii'), the bonds are not adjacent to each other.

(E9)

The absorbent article according to any one of E4 to E8, wherein the color-reducing agent is selected from the group consisting of following items (A)-(E), and any combination thereof:

(A) a complete ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;

(B) a complete ether of (B1) a compound having a chain hydrocarbon moiety and 2-4 hydroxyl groups substituting hydrogens on the chain hydrocarbon moiety, and (B2) a compound having a chain hydrocarbon moiety and 1 hydroxyl group substituting a hydrogen on the chain hydrocarbon moiety;

(C) a complete ester of (C1) a carboxylic acid, alkoxy acid or oxoacid comprising a chain hydrocarbon moiety and 2-4 carboxyl groups substituting hydrogens on the chain hydrocarbon moiety, and (C2) a compound having a chain hydrocarbon moiety and 1 hydroxyl group substituting a hydrogen on the chain hydrocarbon moiety;

(D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety; and (E) a chain hydrocarbon.

(E10)

The absorbent article according to any one of E4 to E9, wherein the color-reducing agent is selected from the group consisting of ($a_1$) a tetraester of a chain hydrocarbon tetraol and same or different fatty acids, ($a_2$) a triester of a chain hydrocarbon triol and same or different fatty acids, ($a_3$) a diester of a chain hydrocarbon diol and same or different fatty acids, ($b_1$) a tetraether of a chain hydrocarbon tetraol and same or different aliphatic monohydric alcohols, ($b_2$) a triether of a chain hydrocarbon triol and same or different aliphatic monohydric alcohols, ($b_3$) a diether of a chain hydrocarbon diol and same or different aliphatic monohydric alcohols, ($c_1$) a tetraester of a chain hydrocarbon tetracarboxylic acid, alkoxy acid or oxoacid with 4 carboxyl groups and same or different aliphatic monohydric alcohols, ($c_2$) a triester of a chain hydrocarbon tricarboxylic acid, alkoxy acid or oxoacid with 3 carboxyl groups and same or different aliphatic monohydric alcohols, ($c_3$) a diester of a chain hydrocarbon dicarboxylic acid, alkoxy acid or oxoacid with 2 carboxyl groups and same or different aliphatic monohydric alcohols, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate and ($e_1$) a linear alkane, and any combination thereof.

(E11)

The absorbent article according to any one of E4 to E10, wherein the top sheet is formed from a nonwoven fabric or woven fabric, and the color-reducing agent is attached to the surfaces of the fibers of the nonwoven fabric or woven fabric.

(E12)

The absorbent article according to any one of E1 to E11, which is a sanitary napkin or panty liner.

(E13)

An absorbent article comprising a liquid-permeable top sheet, a liquid-impermeable back sheet, and an absorbent body between the liquid-permeable top sheet and liquid-impermeable back sheet; wherein the top sheet comprises a color-reducing agent having an IOB of 0-0.35 and a melting point of no higher than 45° C.

(E14)

An absorbent article according to E13 wherein the color-reducing agent further satisfies any one of E5-E10 or any combination thereof.

(E15)

An absorbent article according to E13 or E14 also satisfying any one of E1-E4 or E11-E12 or any combination thereof.

This application claims the benefits of Japanese Application Nos. 2011-102231 and 2011-192148 the entire disclosures of which are incorporated by reference herein.

The invention claimed is:

1. An absorbent article comprising:
a liquid-permeable top sheet, a liquid-impermeable back sheet, and an absorbent body between the liquid-permeable top sheet and liquid-impermeable back sheet,
wherein
the top sheet exhibits a color difference in the range of 39-77, based on the L*a*b* color system and measured from a skin contact surface of the top sheet in a liquid dropping test, and
the top sheet comprises a color-reducing agent having an IOB of 0.00-0.35, a melting point of no higher than 45° C. and a water solubility of 0.00-0.05 g in 100 g of water at 25° C.

2. The absorbent article according to claim 1, wherein the top sheet has, in a liquid residue test, a hemoglobin content represented by absorbance of 0.00-0.10, and a blood cell count of $0\text{-}30\times10^7$/g.

3. The absorbent article according to claim 1, wherein the color-reducing agent is selected from the group consisting of following items (i) and (ii), and any combination thereof:
(i) a hydrocarbon; and
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety,
with the proviso that when 2 or more oxy groups (—O—) are inserted between the compound of (ii), the oxy groups are not adjacent to each other.

4. The absorbent article according to claim 1, wherein the color-reducing agent is selected from the group consisting of following items (i') and (ii'), and any combination thereof:
(i') a hydrocarbon; and
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety,
with the proviso that when 2 or more same or different bonds are inserted between the compound of (ii'), the bonds are not adjacent to each other.

5. The absorbent article according to claim 1, wherein the color-reducing agent is selected from the group consisting of following items (A)-(E), and any combination thereof:
(A) a complete ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;
(B) a complete ether of (B1) a compound having a chain hydrocarbon moiety and 2-4 hydroxyl groups substituting hydrogens on the chain hydrocarbon moiety, and (B2) a compound having a chain hydrocarbon moiety and 1 hydroxyl group substituting a hydrogen on the chain hydrocarbon moiety;
(C) a complete ester of (C1) a carboxylic acid, alkoxy acid or oxoacid comprising a chain hydrocarbon moiety and 2-4 carboxyl groups substituting hydrogens on the chain hydrocarbon moiety, and (C2) a compound having a chain hydrocarbon moiety and 1 hydroxyl group substituting a hydrogen on the chain hydrocarbon moiety;
(D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety; and
(E) a chain hydrocarbon.

6. The absorbent article according to claim 1, wherein the color-reducing agent is selected from the group consisting of ($a_1$) a tetraester of a chain hydrocarbon tetraol and same or different fatty acids, ($a_2$) a triester of a chain hydrocarbon triol and same or different fatty acids, ($a_3$) a diester of a chain hydrocarbon diol and same or different fatty acids, ($b_1$) a tetraether of a chain hydrocarbon tetraol and same or different aliphatic monohydric alcohols, ($b_2$) a triether of a chain hydrocarbon triol and same or different aliphatic monohydric alcohols, ($b_3$) a diether of a chain hydrocarbon diol and same or different aliphatic monohydric alcohols, ($c_1$) a tetraester of a chain hydrocarbon tetracarboxylic acid, alkoxy acid or oxoacid with 4 carboxyl groups and same or different aliphatic monohydric alcohols, ($c_2$) a triester of a chain hydrocarbon tricarboxylic acid, alkoxy acid or oxoacid with 3 carboxyl groups and same or different aliphatic monohydric alcohols, ($c_3$) a diester of a chain hydrocarbon dicarboxylic acid, alkoxy acid or oxoacid with 2 carboxyl groups and same or different aliphatic monohydric alcohols, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate and ($e_1$) a linear alkane, and any combination thereof.

7. The absorbent article according to claim 1, wherein the color-reducing agent has the vapor pressure of 0.00-0.01 Pa at 1 atmosphere, 20° C. or 40° C.

8. The absorbent article according to claim 1, wherein the color-reducing agent has a weight-average molecular weight of no greater than 2,000.

9. The absorbent article according to claim 1, wherein the top sheet is formed from a nonwoven fabric or woven fabric, and the color-reducing agent is attached to the surfaces of the fibers of the nonwoven fabric or woven fabric.

10. The absorbent article according to claim 1, which is a sanitary napkin or panty liner.

\* \* \* \* \*